(12) United States Patent
Grützmacher et al.

(10) Patent No.: US 9,795,539 B2
(45) Date of Patent: Oct. 24, 2017

(54) GRAPHICAL USER INTERFACE

(71) Applicant: Bayer Intellectual Property GmbH, Monheim (DE)

(72) Inventors: Heike Grützmacher, Berlin (DE); Mayk Kresse, Berlin (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/591,954

(22) Filed: Jan. 8, 2015

(65) Prior Publication Data
US 2015/0122830 A1    May 7, 2015

Related U.S. Application Data

(63) Continuation of application No. 12/847,285, filed on Jul. 30, 2010, now Pat. No. 9,089,472.

(30) Foreign Application Priority Data

Jul. 30, 2009 (DE) .................. 2009036004
Oct. 21, 2009 (DE) ............. 10 2009 050 442

(51) Int. Cl.
| | | |
|---|---|---|
| G07F 11/00 | (2006.01) | |
| A61J 7/04 | (2006.01) | |
| G06F 19/00 | (2011.01) | |

(52) U.S. Cl.
CPC .............. *A61J 7/0472* (2013.01); *A61J 7/04* (2013.01); *A61J 7/0481* (2013.01); *G06F 19/3462* (2013.01)

(58) Field of Classification Search
CPC .......... A61J 7/0472; A61J 7/04; A61J 7/0481; G06F 19/3462

(Continued)

(56) References Cited

U.S. PATENT DOCUMENTS 5,392,952 A    2/1995   Bowden
5,691,932 A *  11/1997  Reiner .................. G06F 15/025
                                                   340/309.4

(Continued)

FOREIGN PATENT DOCUMENTS

DE    10035599     2/2002
DE    10217929     11/2003

(Continued)

OTHER PUBLICATIONS

European Patent Office, Written Opinion (with English translation) received in International Patent Application No. PCT/EP2010/004572, Jan. 30, 2012, 10 pages.

(Continued)

*Primary Examiner* — Rakesh Kumar
(74) *Attorney, Agent, or Firm* — Nixon & Vanderhye P.C.

(57) ABSTRACT

In order to monitor the administration of medicament portions Ta in a reliable and simple manner, the invention provides a display device for a dispenser for medicament portions Ta, it being necessary to administer the medicament portions at regularly recurring reference administration times, and the display device comprising a display 1 and an electronic actuation means for the display, characterized in that the display comprises a first visualization means 30, 40 for displaying a first period of time between a first reference administration time and the current time, and the first reference administration time being distinguished in that the medicament portion has not been taken by the first reference administration time.

25 Claims, 23 Drawing Sheets

(58) Field of Classification Search
USPC ...... 128/203.15; 221/5, 15, 2, 69, 92, 8, 17; 340/286.01, 309.16
See application file for complete search history.

(56) References Cited

U.S. PATENT DOCUMENTS

| | | | |
|---|---|---|---|
| 5,850,344 A | 12/1998 | Conkright | |
| 5,871,831 A | 2/1999 | Zeiter et al. | |
| 5,915,558 A * | 6/1999 | Girvetz | A61J 7/0481 206/534 |
| 6,075,755 A * | 6/2000 | Zarchan | A61J 7/0481 221/3 |
| 7,198,172 B2 * | 4/2007 | Harvey | G04F 1/005 221/8 |
| 7,233,228 B2 * | 6/2007 | Lintell | A61M 15/0083 221/8 |
| 7,359,765 B2 * | 4/2008 | Varvarelis | A61J 7/0481 221/265 |
| 7,424,888 B2 * | 9/2008 | Harvey | A61J 7/0481 128/203.15 |
| 7,896,192 B2 * | 3/2011 | Conley | A61J 7/0472 221/15 |
| 8,149,096 B2 * | 4/2012 | Metry | A61J 7/0481 215/228 |
| 8,441,893 B2 * | 5/2013 | Stephens Stauffer | G04F 10/00 368/10 |
| 8,536,987 B2 * | 9/2013 | Metry | A61J 7/0481 215/228 |
| 9,089,472 B2 * | 7/2015 | Ranze | A61J 7/0472 |
| 2002/0118604 A1 * | 8/2002 | Sharma | G04F 3/02 368/10 |
| 2003/0006242 A1 | 1/2003 | McKinney et al. | |
| 2004/0008589 A1 * | 1/2004 | McMillan | G07C 1/00 368/223 |
| 2005/0252924 A1 | 11/2005 | Pieper et al. | |
| 2008/0142472 A1 * | 6/2008 | Metry | A61J 7/0481 215/228 |
| 2009/0065522 A1 | 3/2009 | Benouali | |
| 2010/0214877 A1 * | 8/2010 | Turk | A61J 7/0481 368/10 |
| 2015/0122830 A1 * | 5/2015 | Ranze | A61J 7/0472 221/2 |

FOREIGN PATENT DOCUMENTS

| | | |
|---|---|---|
| DE | 202004012232 | 10/2004 |
| DE | 202004012232 u1 * | 11/2004 |
| DE | 102004023641 | 12/2005 |
| WO | 03/088891 | 10/2003 |
| WO | 2005/110335 | 11/2005 |

OTHER PUBLICATIONS

European Patent Office, International Search Report (with English translation) received in International Patent Application No. PCT/EP2010/004572, Feb. 3, 2011, 7 pages.
International Bureau of WIPO, International Preliminary Report on Patentability received in International Patent Application No. PCT/EP2010/004572, Jan. 31, 2012, 6 pages.

* cited by examiner

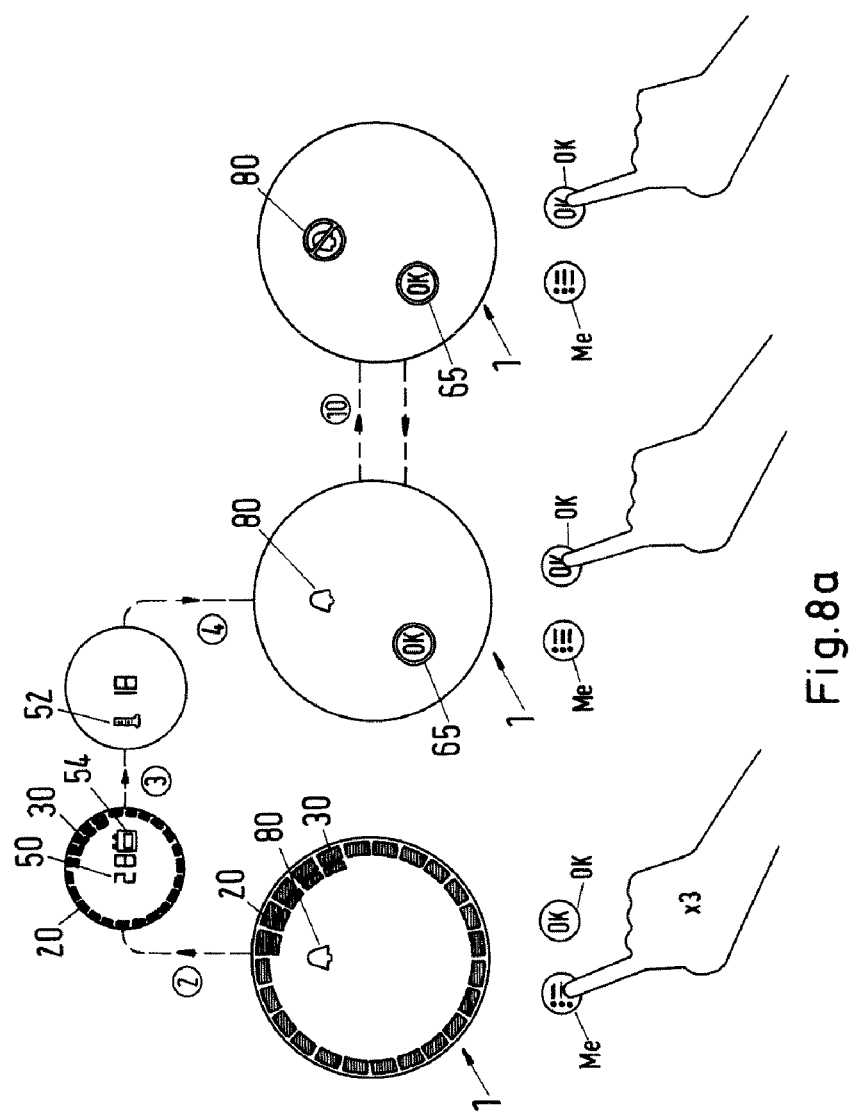

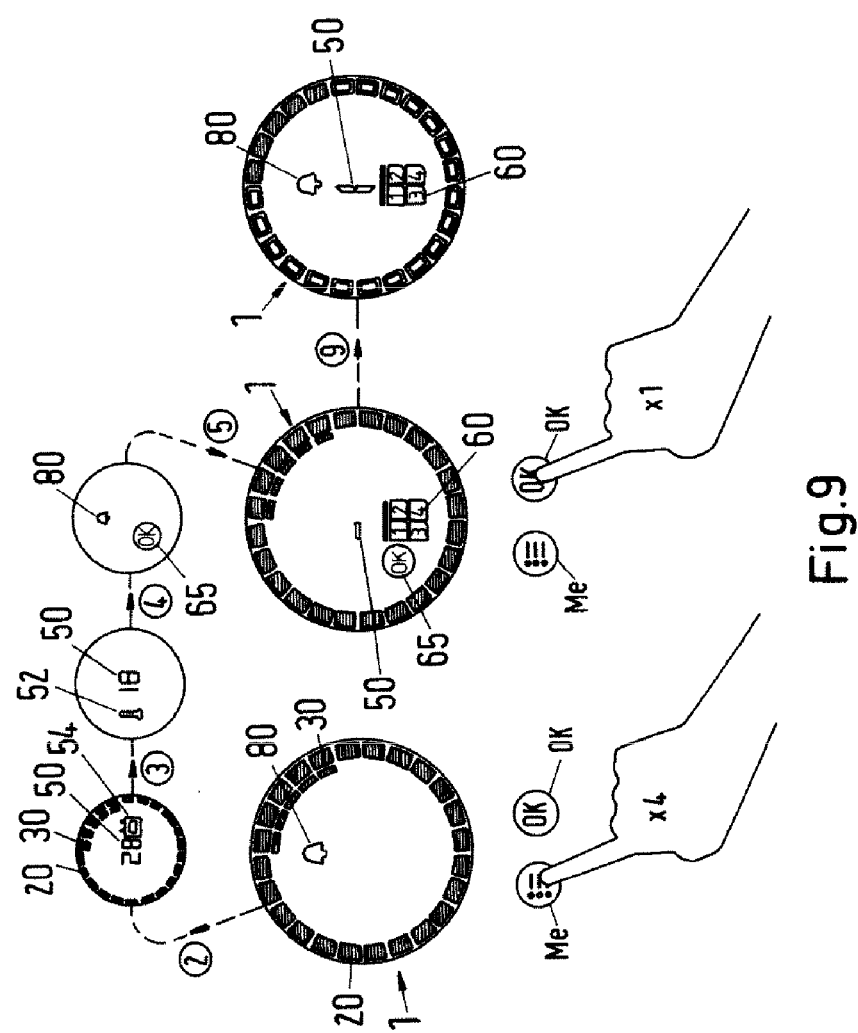

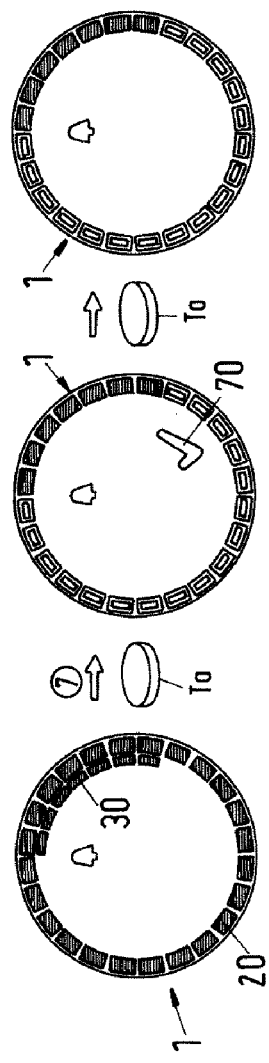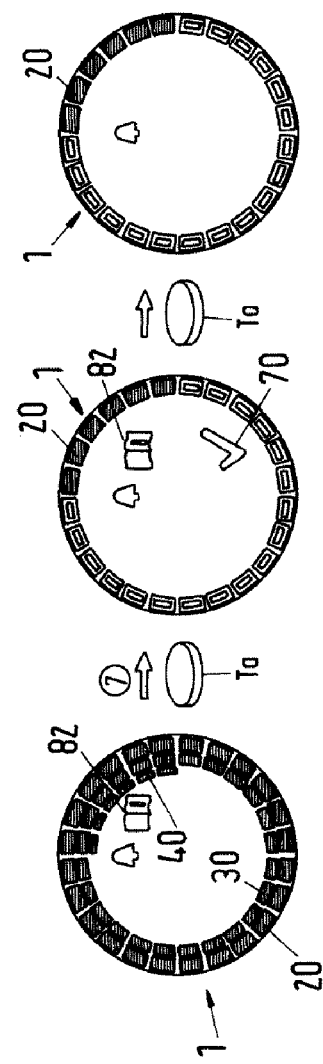

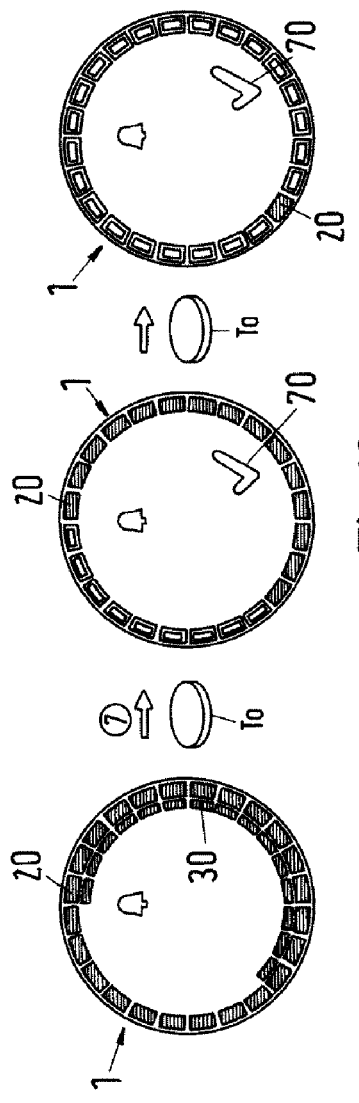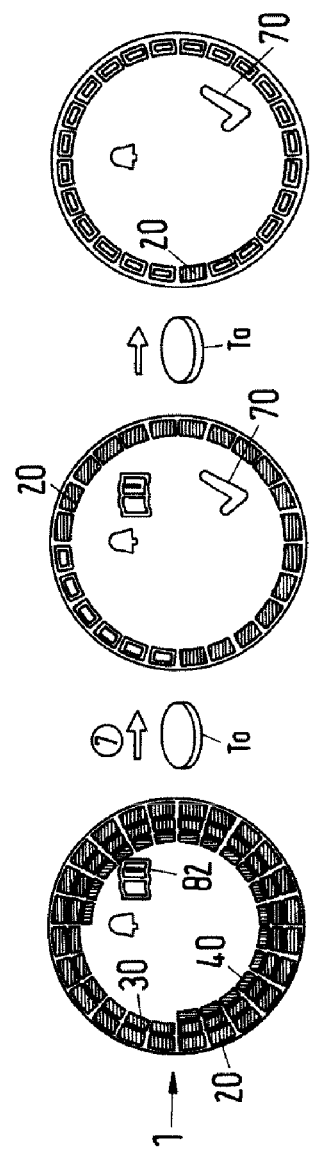

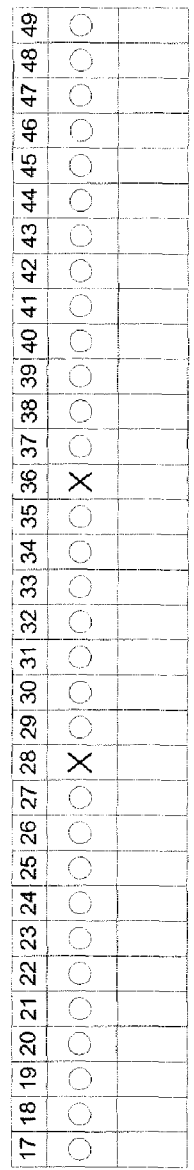 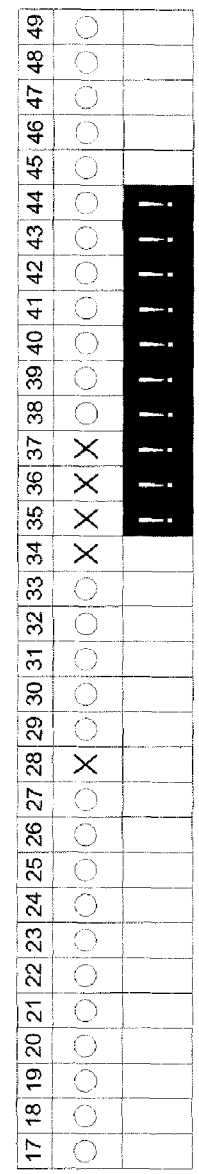
(a) (b)
Fig. 22

GRAPHICAL USER INTERFACE

The present invention relates to a display device for a dispenser for medicament portions, it being necessary to administer the medicament portions at regularly recurring reference administration times, and the display device comprising a display and an electronic actuation means for the display. The present invention also relates to the use of this display device for monitoring the administration of medicament portions, in particular hormone preparation portions, primarily contraceptive portions, from a dispenser.

Medicaments have to be taken regularly and, as far as possible, at a predefined time or within a predefined period in order to be able to guarantee their efficacy. Therefore, there has been no lack of attempts to create aids to provide reminders to administer the medicament. Very common aids for people who have to take several medicaments on a daily basis are boxes which are divided into several compartments which are manually filled with the medicaments for the respective administration period, for example for administration in the morning, administration at midday and administration in the evening. Therefore, the person taking the medicaments can respectively monitor whether a medicament portion has already been taken or not at the respective time. However, these aids are susceptible to faults because the person obviously, for example, also has to remember to take the medicament portion at the prescribed times or in the periods intended for this purpose, and to actually fill the boxes with the medicament portions in the first place.

Therefore, display apparatuses which are intended to provide an automatic administration reminder have been developed for administering medicaments. By way of example, DE 100 35 5999 A1 describes a pill box with an integrated timer. The pill box comprises a plurality of compartments for accommodating pills, which compartments each have an associated light-emitting diode. The timer comprises a digital display and also operator control buttons for programming the said timer. One of the light-emitting diodes is actuated at the respectively pre-programmed time at which the pills contained in the associated pill compartment are to be administered, and therefore the user knows which pills are to be taken. Acoustic and mechanical signal transmitters are also provided.

Furthermore, DE 20 2004 012 232 U1 describes a so-called pill clock. This pill clock firstly has a pill box which is combined with a digital clock. The intention is for the user to carry around the tablets to be taken and be reminded to administer the said tablets by the digital clock. The pill box has six compartments for the tablets. The digital clock is provided with a digital display for the actual time and six further digital displays which, in various modes, provide a reminder to administer the tablets in the six compartments of the pill box. In one mode, the pill clock provides a reminder to respectively administer a tablet using a countdown display. The user can also be provided with an acoustic administration reminder. The pill clock can be worn on the wrist like a wristwatch.

Furthermore, DE 10 2004 023 641 A1 discloses an apparatus having means for connection to a contraceptive pill blister. The apparatus serves to assist correct administration of contraceptive pills over the entire menstrual cycle and is also intended to take into account the non-administration phase too. To this end, the apparatus is designed such that a blister containing the contraceptive pills can be connected to the apparatus, for example by means of a clip or a pocket, and possibly a detection means for insertion of the blister into the apparatus and/or for the removal of the blister from the apparatus is additionally provided. Detection means for monitoring the filling level of the tablet units can also be located in the blister. By way of example, breaking open the foil over a blister in order to remove a contractive pill from a tablet unit can activate a timer. The apparatus has a display in the form of a digital clock which displays the period remaining until the start of an alarm signal. Alarm signals can be emitted by means of loudspeakers, vibrators or light-emitting diodes or else the display. The display also shows the user which day of her cycle she is currently on.

U.S. Pat. No. 5,871,831 A also exhibits an apparatus which comprises a computer with a plug-type contact strip for insertion of a tablet blister. The tablet blister is designed in a suitable manner such that conductor tracks are located at those points on the foil which will be breached when a tablet is removed, and therefore the said conductor tracks will be severed when the foil is breached, the conductor tracks coming into electrical contact with the plug-type contacts located in the plug-type contact strip when the blister is inserted into the plug-type contact strip in the computer. As a result, removal of a tablet can be automatically registered. The computer has a digital display for the current time and/or the time at which a tablet is next to be administered. An acoustic signal or LED can also provide a reminder to administer a tablet. A first one of the LEDs serves to indicate that a tablet is to be taken, a second LED serves to indicate that administration would still be too early, and a third LED serves to indicate that the administration time has already been exceeded.

Furthermore, DE 102 17 929 A1 discloses an apparatus for dispensing tablets. This apparatus serves to accommodate blisters and has pushbuttons for pushing a tablet out of the blister as well as means for setting administration times and also means for displaying the administration times. The apparatus provides a reminder to administer a tablet over a preset administration time. Alarm symbols on an LCD display serve for this purpose. The apparatus also automatically registers removal of a tablet.

Although the above-described apparatuses are suitable for providing an automatic reminder of the administration time of medicament portions, a variety of different indicator and alarm means serve this purpose in the described dispensers. In individual cases, a reminder is repeatedly provided for the possibly initially forgotten or deliberately missed administration of a medicament portion. However, the user is not provided with complete knowledge of the administration status with this information. For example, it is generally not necessary to take a medicament portion at a precisely defined time. Rather, it suffices to take the medicament portion within a time interval. Although DE 20 2004 012 232 U1 states, to this end, that an alarm can also be repeated, it being possible for the user to set how often and at which intervals the alarm is to be repeated, the said document does not state the relationship between the alarm being repeated and the actual tolerance of the time being exceeded and of the time actually being exceeded.

Proceeding from the above, it is an object of the present invention to provide a display device for the administration of medicament portions which are contained in a dispenser, with which display device the known disadvantages are eliminated and with which the intention is, in particular, to ensure increased compliance when administering medicament portions. The primary intention is to enable the user to quickly and easily identify the current status of administration of medicament portions. In particular, a further intention is to ensure that the administration of, in particular, hormone preparations, primarily contraceptives, is particularly reliable by the necessary information about the current administration status being optically displayed to the user at a glance. A further intention is to provide the user with a proposal for possible remedies quickly, simply and without the said user having to laboriously search through the documentation in the event of incorrect operation and also if the user forgets to take the medicament portions. Increased compliance in terms of medicament administration should also be achieved by incorrect operation being largely precluded, for example in the case of the user accidently taking more than one medicament portion, but this administration not being taken into account in the administration log, or in the case of a medicament portion not being taken but administration erroneously being registered in the administration log. A further intention is to ensure the reliability of administration in the long-term too, that is to say when medicaments are administered over a long period.

This object is achieved by the display device according to claim 1 and also by the use of the display device according to claim 23. Preferred embodiments of the invention are indicated in the dependent claims.

The display device according to the invention serves to monitor the status of administration of medicament portions by a user. The primary intention is to display the status of administration of hormone preparations and, very particularly, of steroid hormone preparations, for example for contraception. However, a further intention is for it to be possible for the administration of portions of other medicaments, for example hormone preparations for hormone replacement therapy, to be monitored in a simple and reliable manner. For example, the display device can be used to monitor the status of medicament portions for treating all chronic diseases. The use of the display device is very particularly important when the medicament portions are to be administered at regularly recurring reference administration times. Therefore, the primary intention of the display device according to the invention is to serve to monitor the status of the administration of contraceptives. In this case, the medicament portions have to be taken in a regular administration regime, specifically once a day, an interruption phase of several days' duration always following an administration phase of several days' duration. If the prescribed administration times are not followed, the desired contraceptive action may not take effect.

In order to achieve the aim according to the invention, the display device has a display and an electronic actuation means for the display. In a manner according to the invention, the display comprises a first visualization means for displaying a first period of time between a first reference administration time and the current time, the first reference administration time being distinguished in that no medicament portion has been taken up to the first reference administration time (even though this was intended to be the case).

Within the meaning of the present invention, reference administration times are understood to be times at which the medicament portions should ideally be taken, that is to say, for example in the case of medicament portions which are to be taken daily, at, for example, 7:00 or 9:00 or at another fixed time on each day, it sufficing in virtually all cases, however, for the purpose of taking a medicament in due time, for the medicament portion to be taken within a time interval which includes the reference administration time. The administration interval may last, for example, from a time 12 hours before the reference administration time up to a time, for example, 2 or else 24 hours after the reference administration time. In the case of medicament portions which are to be taken, for example, once daily, such a reference administration time and the administration interval are to be determined on each day. The reference administration time is preferably calculated from the time at which a medicament portion is first removed (from a medicament dispenser), in particular preferably in an administration cycle, and the prescribed repetition rhythm for administration. The respective reference administration times are then calculated from the respective time intervals which are produced from the repetition rhythm and the time at which a medicament portion is first removed from the dispenser, this time again being identical to the time of first administration of a medicament portion. Therefore, the reference administration times in the case of medicament portions which are to be taken once per day are, with a calculation method of this kind, in each case n x 24 hours (n is an integer) after the first removal of the medicament portion from the dispenser. If, in the case of this calculation method of the reference administration times in the case of a medicament portion which is to be taken once daily, a first medicament portion is, for example, removed from the dispenser, and therefore has been taken by the user, at 12:00 on the first day, this time (12:00) on each following day is a reference administration time and therefore further reference administration times occur at 12:00 on each further day following the first day, the intention being for the medicament portions to ideally be taken at the said reference administration times. Analogously, in the case of a medicament which is to be taken twice per day, for example when first removal and therefore first administration has taken place at 7:00 and second administration has taken place 12 hours after that, the reference administration times are calculated to be at 7:00 and 19:00 on each following day. In principle, the reference administration times can also be calculated differently starting from the first removal of the medicament portion from the dispenser: for example, a reference administration time can be calculated from the last, for example three, actual administration times.

The display device therefore has a display for the first reference administration time, that is to say an administration time at which the medicament portion should be taken, being exceeded, but the user accidently or else intentionally failing to take the medicament portion up to this first reference administration time.

Since the display device according to the invention has the abovementioned first visualization means for displaying the first reference administration time being exceeded, comprehensive monitoring of the administration status of the medicament is possible: the display of a time being exceeded allows the user or else a doctor to possibly initiate corrective measures to compensate for the lack of administration. Furthermore, the user can also immediately identify when the time interval for administration elapses if he/she knows the time interval in which the medicament portion has to be taken. The time interval can, of course, also be separately displayed in the visualization means, and therefore the user can identify at a glance whether he/she can still take the medicament portion in due time, that is to say within the time interval, despite the first reference administration time having been exceeded.

The display device according to the invention is preferably advantageous for the administration of contraceptives and, in this case, very particularly in cases in which the user follows a so-called flexible administration regime. Contraceptives typically have to be taken once daily, with, in the case of conventional administration regimes, a medicament portion being taken daily during an administration phase of 21 days and this then being followed by a 7-day-long interruption phase. This administration cycle is then repeated again. As an alternative, the administration phase can also last for 24 days and the interruption phase for 4 days. It has also already been proposed to take contraceptive preparations in accordance with a so-called flexible administration regime. In this case, the administration phase lasts at least 24 days (compulsory administration phase) and at most, for example, 120 days. A decision about the duration of the administration phase is left to be made by the user within the said limits, that is to say, after the compulsory administration phase has elapsed, the user herself can decide whether to initiate the interruption phase. However, the said user must do this before the maximum time of the flexible phase elapses, that is to say before 120 days elapse in the cited case. The flexible administration phase is typically followed by an interruption phase of 4 days. The decision of the user to initiate the interruption phase may in this case be triggered by breakthrough bleeding and/or spotting occurring on 3 consecutive days immediately prior.

Monophasic contraception preparations usually contain an oestrogen and a gestagen as pharmaceutically active substances in each medicament portion, specifically the same quantity of the oestrogen and of the gestagen in each daily medicament portion. Monophasic contraception preparations of this kind can be used in a flexible administration regime as described above. A person skilled in the art is familiar with which compounds can be used as oestrogen and gestagen in a monophasic contraception preparation. The oestrogen contained almost without exception in all contraception preparations is ethinylestradiol. The list of gestagens used in contraception preparations is long. Only levonorgestrel, cyproterone acetate, norethisterone, gestodene, desogestrel, dienogest and drospirenone are cited by way of example here.

According to one embodiment of the invention, the display apparatus according to the invention is used for monitoring the administration of medicament portions from a dispenser, with the medicament portions being the daily medicament portions of a monophasic contraception preparation as described above and the contraception preparation being administered in a flexible administration regime, likewise as described above.

In one embodiment, ethinylestradiol is used as the oestrogen and drospirenone or dienogest is used as the gestagen.

In a particular embodiment, ethinylestradiol is used as the oestrogen and drospirenone is used as the gestagen. According to a further, preferred embodiment, 20 µg of ethinylestradiol and 3 mg of drospirenone are contained in each medicament portion.

If the user has failed to take a medicament portion, she can at least use the situation of exceeding the administration time interval as a transition to an interruption phase if the administration phase has already lasted for at least 24 days (before expiry of the administration phase, an interruption phase would lead to contraception no longer being guaranteed). In particular, this first period of time for the time overrun after the first reference administration time can, in this case, be calculated as a period within the interruption phase. In this case, the present invention also serves to provide the user with a simple way of deciding to changeover from the administration phase to the interruption phase: if, for example, the administration time interval is exceeded, the user can decide to start an interruption phase, so that regular administration can again be started in the correct manner after the interruption in administration. With the conventional apparatuses for monitoring administration, this would only be possible if the user were to theoretically monitor compliance with the administration regime with the highest possible level of self-organization. However, since the user would have to keep track of the situation of the time being exceeded in this case, this is not readily possible under customary conditions which are subject to everyday distractions.

Therefore, displaying the situation of the first reference administration time being exceeded can provide a greater level of reliability in the case of administration of medicament portions.

In one preferred embodiment of the invention, the display additionally comprises a second visualization means for displaying a second period of time between a second reference administration time and the current time. In this case, the second reference administration time is distinguished in that it is in a predefined administration time interval and one medicament portion has been taken in the predefined administration time interval. The second period of time lasts at most up to the first reference administration time which chronologically follows the second reference administration time. That is to say, when the entire scale of the second visualization means is utilized, the display extends over the entire period between the second reference administration time and the first reference administration time if the medicament portion has not been taken by the first reference administration time or is taken precisely at this time. If the medicament portion has not been taken by the time the first reference administration time has been reached, the first visualization means, which then displays the following first period of time since the first reference administration time, is started. The elapsed second period of time between the second reference administration time and the first reference administration time preferably remains displayed in this case, but can also be cleared in cases in which, for example, the period which has already elapsed since the second reference administration time is not displayed, but the period still remaining until the next reference administration time is displayed.

Like the first reference administration time, the second reference administration time also represents a time in the administration regime at which a medicament portion should ideally be taken. The only difference is that a medicament portion has been taken in the case of the second reference administration time and not in the case of the first reference administration time. In this respect, the abovementioned explanations for reference administration times apply here too.

The second period of time, which has passed since the most recent second reference administration time of a medicament portion in the event of correct medicament administration, is displayed by the second visualization means. Therefore, the user can be provided with additional information about the current status of administration of medicament portions in the event of the administration instructions being followed correctly. Since, in the case of administration being performed as instructed, the user can track the period which has passed since the most recent second reference administration time, the said user can prepare for the next medicament administration operation.

The second visualization means is preferably started by first removal of a medicament portion from the dispenser in an administration cycle. The second reference administration time and therefore also the first reference administration time are therefore preferably established and defined for a current administration cycle. An administration cycle is established, for example, by all of the administration processes during a period of illness. In the case of continuous administration, for example for hormone replacement therapy, the administration cycle is likewise characterized by first removal and, in the case of contraception, by an administration phase and an interruption phase, before a new administration phase begins. The reference administration times are therefore defined with first removal of a medicament portion from a dispenser in an administration cycle.

Since the reference administration times are each preferably defined only for a single administration cycle, the user can redefine the reference administration times in a new cycle. This is advantageous when the originally selected reference administration time has turned out to be impractical for the user and the user wishes to change the reference administration time.

While the second reference administration times are defined by first removal of a medicament portion from the dispenser, the first reference administration times are found by no medicament portion having been taken by the first reference administration time which chronologically follows the second reference administration time. In this case, the first visualization means is therefore started by the first reference administration time being reached, that is to say when no medicament portion has been taken by this first reference administration time. In this case, the first period of time which has passed since the first reference administration time follows the illustrated second period of time since the second reference administration time. In this case, the first and the second visualization means show, at the same time, the period since the most recent second reference administration time, that is to say since a reference administration time which is characterized in that it is in a predefined administration time interval in which the medicament portion has been taken and therefore correct administration has taken place.

When a medicament portion is taken, a new second reference administration time is generated. If, in this case, only the second visualization means has displayed the second period of time since the (previous) second reference administration time (because the nominal period for administration of the medicament portion has not yet elapsed), the display of the second period of time is cleared and a new second period of time is displayed, this showing the time difference between the current time and the new second reference administration time. In the latter case, this second period of time is negative, that is to say initially the second period of time between the current time and the new second reference administration time which has not yet been reached is displayed. As an alternative, the second period of time can also be displayed in the form of the period until the next reference administration time, which period has not yet elapsed, in this case. Since the second period of time until the next reference administration time is longer than an administration period, this period of time which has not yet elapsed is preferably displayed in two scale parts: a first scale part which shows the period remaining until the previous reference administration time, and a second scale part which corresponds to the regular second period of time. Therefore, during the further course, the region which goes beyond regular display of an administration period is then preferably initially successively switched off, and only then is the regular region successively switched off.

If the next reference administration time had already been reached at the time of removal of a medicament portion and a first reference administration time had therefore been generated, so that the first visualization means also displays a first period of time since this (newly generated) first reference administration time, the display of the first period of time is cleared by the removal of a medicament portion, and a new second period of time is displayed, this showing the time difference between the current time and the new second reference administration time. Since, in this case, the medicament portion was first taken after the next reference administration time had already passed without a medicament portion having been taken, the second visualization means will display a second period of time, which has already passed, since the new second reference administration time. In one possible method, the second reference administration time is, in cases in which the previous second reference administration time had been considerably exceeded, set to a new second reference administration time which is shifted by two administration periods between in each case two successive reference administration times and not only by one, that is to say, in this case, medicament administration is interrupted once. As an alternative and with preference, the display is, however, shifted by only one removal period when a medicament portion is removed, so that the user is required to remove yet a further medicament portion in order to restart the correct administration rhythm.

In a further preferred embodiment of the invention, a new second reference administration time is generated in the case of premature removal of a medicament portion only when the medicament portion is, at the earliest, in the administration time interval. If the removal time is still before the beginning of the administration time interval, the removal is not taken into consideration as medicament administration, and therefore the previous display of the second period of time remains since a new second reference administration time is not generated in this case. If, in contrast, a medicament is taken within the administration time interval before the second reference administration time is reached, a new second reference administration time is generated. In this case, a new negative second period of time is initially displayed, that is to say the period of time between the current time and the later new second reference administration time. A new second reference administration time is, as explained above, also generated when the medicament is first taken after the administration time interval elapses.

In a further preferred embodiment of the invention, the first visualization means is arranged in at least one first display region and the second visualization means is arranged in at least one second display region of the display.

It is particularly preferred if the at least one first display region and the at least one second display region are adjacent to one another.

It is also preferred if the first visualization means is formed by at least one first indicator element.

It is further preferred if at least two first indicator elements are provided, and the first indicator elements are successively switched on as time progresses. In this case, the first indicator elements represent the progress of time graphically and not in the form of a numerical display.

The first indicator elements can also represent a numerical display. For example, the numerical display can display the number of medicament portions still to be taken.

Either the first indicator elements which provide a graphical representation or the first indicator elements which display numerals, or both, can be present.

It is further preferred if the second visualization means is formed by at least one second indicator element.

It is further preferred if at least two second indicator elements are provided and the second indicator elements are successively switched on or successively switched off as time progresses. Therefore, the second indicator elements represent the progress of time preferably graphically and not in the form of a numerical display. If the indicator elements are successively switched off as time progresses, all the indicator elements or at least the indicator elements for time periods which remain until the next reference administration time are initially displayed and these are then switched off as time progresses.

The graphical displays provide quick, simple and fault-free identification of the first and second periods of time.

It is further preferred if each of the at least one first and/or each of the at least one second indicator elements corresponds to periods of time of equal magnitude, for example 1 hour, in the case of a graphical display.

A particularly advantageous refinement of the display of the first and second periods of time is provided by each of the at least one first indicator elements forming a segment in at least one ring and/or by each of the at least one second indicator elements forming a segment in at least one second ring. Therefore, the progression of time of the respective periods of time can be identified upon first glance, like on a clock which displays the time in an analogue manner.

The ability to identify the progression of time in an easy and quick manner is further improved by the at least one first ring for the at least one first indicator element and the at least one second ring for the at least one second indicator element being concentric to one another. If, for example, the second visualization means has indicator elements in an outer ring and the first visualization means has indicator elements in one or more inner rings, the indicator elements which form the rings will gradually fill the rings from outside inwards as time progresses. As an alternative, the second indicator elements can also be arranged in a first outer ring together with first indicator elements, and further second indicator elements can be arranged in further rings which are arranged further inwards.

For example, each of the first and second rings can in each case symbolize a period of 1 day. If the rings are made up of segments of a ring, each of the segments of the ring can symbolize 1 hour, and therefore there are in each case 24 segments of a ring in one ring. It goes without saying that the periods for the rings and for the individual segments of a ring can be subdivided in other ways. The indicator elements may be substantially rectangular or else assume any other desired shape. For example, the said indicator elements may be circular or star-shaped. As an alternative, other indicator displays, for example bars or arrows, which increase in size in steps or continuously, in a scale or else a completely different representation which shows the progression of time at a glance, can of course be used instead of segments of a ring. A numerical display numerically displays the progression of time by providing time details.

In one particularly advantageous embodiment of the invention, the first indicator elements of the first visualization means and the second indicator elements of the second visualization means each symbolize time periods which have elapsed or which are still to elapse. As in the above-mentioned embodiment, these first and second indicator elements can be arranged in the form of segments of a ring in one or more rings. In this case, segments of a ring which are flat can be used for the first visualization means, and segments of a ring which represent only frames can be used for the second visualization means. It is particularly advantageous if the second indicator elements of the second visualization means are shown in the form of a surrounding frame for the flat representations of the first indicator elements of the first visualization means. Therefore, the second indicator elements of the second visualization means are located in the same ring as the first indicator elements of the first visualization means in this case. However, as already described above, further first indicator elements of the first visualization means can, of course, also be provided, these being located in further rings in which there are no second indicator elements of the second visualization means. For example, the first indicator elements and the second indicator elements together form an outer ring and the further first indicator elements form a further inner ring. As already illustrated, at least some second indicator elements can also possible on the ring which is shifted inwards. Other rings, for example rings which are situated even further inwards, for indicator elements are also feasible in principle.

In a further advantageous refinement of the last-described embodiment of the invention, the second indicator elements of the second visualization means indicate the progression of time since the second reference administration time by successively switching off second indicator elements which are initially displayed. That is to say, when a medicament portion is removed and therefore a second reference administration time is established, all the second indicator elements are initially displayed, that is to say the indicator elements for time periods until the next (not yet reached) second reference administration time are illustrated. If, however, the second reference administration time has already elapsed when the medicament portion is removed, not all of the second indicator elements of the second visualization means are displayed when a medicament portion is removed, but rather only those which correspond to the period of time still remaining until the next reference administration time. In this case, the first indicator elements of the first visualization means can, as in the case described above, be successively displayed as the time overrun increases. Therefore, the second visualization means immediately initially indicates, after removal of a medicament portion, the period of time remaining until the next reference administration time, while the first visualization means immediately indicates, in the case of a subsequent time overrun, the time overrun which has already occurred.

Furthermore, the first visualization means can comprise a first zone and a second zone which is spatially delimited from the first zone, the second zone serving to display that a predefined third period of time has been exceeded. If the first reference administration time is exceeded by a predefined third period of time, without the user taking a medicament portion, the incorrect administration may have serious consequences. This will then be indicated by, for example, a representation in a different (signal) colour of the first indicator elements in the second zone which is spatially delimited from the first zone. For example, the indicator elements in the first and the second zone may each represent a period of one day, so that it is possible to show, in total, that the first reference administration time has been exceeded by 2 days. In principle, an overrun of the first reference administration time by a shorter or longer period is, of course, also possible.

In a further preferred embodiment of the invention, a display for the number of medicament portions contained in the dispenser is additionally provided. The display can be, for example, a digital numerical display. This provides the user with additional security for administering the medicament portions since this guarantees that the user can always ensure that at least one medicament portion is always available. The user can therefore make adequate arrangements for a forthcoming journey.

In a further preferred embodiment of the invention, a display for the number of medicament portions which have already been taken in an administration cycle is additionally provided. This information can likewise be displayed by a numerical display. It is therefore possible for the user to monitor the course of administration of medicament portions. In the case of contraception with a flexible administration regime, the user can therefore make the decision as to when to initiate an interruption phase after an administration phase in which she has taken 24 portions of contraceptive (compulsory administration phase) has elapsed. This is important in terms of the restrictions when making a decision about initiating the interruption phase since the interruption phase must not be initiated before the compulsory administration phase has started and has to be initiated at the latest after a total of, for example, 120 contraceptive portions has been administered.

In a further preferred embodiment of the invention, a display for interruption in administration is additionally provided. This can be realized by a symbol which is suitable for this purpose. The user of contraceptives will therefore be shown that an interruption in administration has been initiated and that no medicament portions should be currently taken. The interruption phase usually lasts for 4 days in a flexible regime. After the interruption phase has elapsed, an administration phase is again initiated in a new administration cycle. To this end, the user removes a first medicament portion in this new administration cycle, and thus triggers the second visualization means and thus also defines the new reference administration times.

It goes without saying that the actuation means for the display can also contain a logic system according to which initiation of the interruption phase is prevented if 24 medicament portions have not yet been taken in the current administration cycle (compulsory administration phase). This can be displayed, for example, by the symbol indicating the interruption in administration not appearing or being struck through. A warning signal which can be optically, acoustically and/or haptically perceived can also be displayed.

Apart from the user being able to move from the administration phase to the interruption phase on her own initiative when the medicament is a contraceptive which can be administered in a flexible regime and when the said user is no longer in the compulsory administration phase, provision may be made for the display device to automatically initiate the interruption phase when the last administration of a medicament portion took place a minimum period of time ago. For example, provision may be made for the interruption phase to be automatically initiated when the second reference administration time was 72 hours ago. By changing over to the interruption phase, it is possible, in this case, to currently display on the display that the interruption phase has already lasted for 48 hours. Automatic transition of this kind is readily possible when the user has already reached the flexible administration phase. However, this automatic transition can also take place, in a possible embodiment of the invention, when the user is still in the compulsory phase. However, in this case, a reliable contraceptive action is no longer provided. However, the aim of automatic transition to the interruption phase is again to achieve a correct administration regime.

In a further preferred embodiment of the invention, the display for interruption in administration includes a display for the number of days for which administration is interrupted. This display can in turn be formed as a digital numerical display.

In a further preferred embodiment of the invention, the first or the second visualization means display, during the interruption in administration, the period of time which has elapsed between two reference administration times. These reference administration times are the times which, like the first reference administration time and the second reference administration time, are calculated from the time at which a medicament portion is first removed in an administration cycle, and which are in the period of interruption in administration. Therefore, the progression of time can also be tracked during an interruption in administration, so that the user always has a good overview of the status of the interruption phase in this phase.

In a preferred embodiment, provision may also be made for the user to be shown that two medicament portions have to be taken when the second reference administration time was longer than 2 administration periods, but preferably not longer than 3 administration periods, ago, that is to say, in this case, the user removes all (both) medicament portions which he/she has failed to take to date. In order to allow the user to take all medicament portions which he/she has failed to take in such cases, provision may be made, for example, for the display of the time overrun (by the first visualization means) to be cleared when only one medicament portion is removed only during the period which corresponds to the removal of an individual medicament portion, that is to say during the period which corresponds to one day in the case of daily administration of a medicament portion. Therefore, when only one medicament portion is initially removed, a remaining time overrun display always remains which, however, is now 24 hours shorter after the removal of this medicament portion. The display for the time overrun is completely cleared and the display by the second visualization means, which display displays the period since the second reference administration time, is also at least partly cleared only when a second medicament portion has also been taken.

If the medicaments are contraceptives which are taken in a flexible administration regime, a procedure of this kind can, in principle, be provided both if the user is in the compulsory phase or in the flexible phase. If a time of up to 48 hours is exceeded (that is to say a period of up to 72 hours since the second reference administration time), there is preferably still no automatic transition from the administration phase to the interruption phase. If, however, the period of time since the second reference administration time is 72 hours or more, that is to say 3 or more medicament portions should have been taken and have not been taken, the display performs an automatic transition to the interruption phase. If the user is in the compulsory phase in this case, the display preferably additionally displays that further prevention means also have to be used (back-up contraception) since effective contraception is no longer provided under these conditions. In the case of such an event, provision may be made for the user to be warned by an optical and/or acoustic and/or haptic alarm signal and to additionally preferably be provided with an optical indication to use an additional prevention means in addition to further administration of the medicament portions.

Additional contraceptive measures are in each case required when reliable contraception is no longer guaranteed. Reliable contraception is guaranteed only under the following condition:

in the case of missed administration of medicament portions on a single day or on several days within a period of a maximum of 7 days of irregular administration which is characterized in that, before the first day of this period on which no medicament portion has been taken, medicament portions have been taken without interruption over at least 7 days, and the last day of this time period on which no medicament portion was taken is again followed by an at least 7-day period of time in which medicament portions are taken without interruption.

In other words, a phase with irregular administration on several days between two phases each with at least 7-day regular administration must not last longer than 7 days in order to provide reliable contraception. Otherwise, additional contraceptive measures have to be taken.

It has been found that lowering the plasma level of the active substances in the contraceptive does not lead to a risk to contraceptive protection in these cases.

If, however, the abovementioned conditions are not met, additional contraceptive measures are required. The first day on which additional contraceptive measures are required is a day with missed administration which follows the abovementioned 7-day period of irregular administration with uninterrupted administration of medicament portions within less than 7 days. At this moment, there is a missed administration period of more than 7 days, calculated from the first day of missed administration until the last day of missed administration, without this missed administration period having been interrupted by a period of 7 days of uninterrupted administration of medicament portions.

In other words, a phase of at least 7 days of uninterrupted administration of medicament portions has to follow a phase of irregular administration on up to 7 consecutive days in order to maintain the contraceptive action.

The need for additional contraceptive measures lasts until a period of at least 7 days of uninterrupted administration has again elapsed.

The above rules are independent of whether no tablets are taken on days on which, according to the prescribed administration regime, tablets are to be taken (administration phase) or whether these days occur in an interruption phase, that is to say that no tablets are to be taken on these days according to the administration regime. In other words, days on which no tablets are to be taken according to the administration regime are treated like days with missed administration.

The display device is preferably designed in such a way that, under the abovementioned conditions, it displays, on each day, whether additional contraceptive measures are required. To this end, a warning symbol for lack of contraception, for example an exclamation mark ("!"), can automatically appear on the display. According to the above explanations, this warning symbol appears under the following conditions:

a) a missed administration period is produced, this being characterized
   i) in that the missed administration period follows a first administration period of at least 7 days of uninterrupted administration of medicament portions,
   ii) in that the missed administration period is again followed by a second administration period of at least 7 days of the requisite uninterrupted administration of medicament portions,
   iii) no medicament portion being taken on at least one day in the missed administration period,
   iv) in that no period of at least 7 days of uninterrupted administration is included in the missed administration period,
   v) in that no medicament portion is taken on the first and last day of the missed administration period, and
   vi) in that the missed administration period lasts longer than 7 days;
b) the first day on which the warning symbol appears is the 8th day of the missed administration period;
c) the last day on which the warning symbol appears is the 7th day of the second administration period which follows the missed administration period and involves uninterrupted administration of medicament portions.

In a further preferred embodiment of the invention, the display device is a digital display device. In particular, the display device may be an LCD display device. For example, an OLED display may be provided. As an alternative, any other desired technologies can be used.

Furthermore, the display device can also contain further indicator elements for other functions, for example a symbol for a low battery charge state, a symbol for displaying whether an acoustic warning signal is switched on or switched off, a symbol for advising the user to consult the operating instructions, a symbol for indicating that the digital numerical display is displaying the number of medicament portions still in the dispenser, a symbol for indicating that there is a low level of medicament portions, a symbol for indicating that the digital numerical display is displaying the number of the medicament portions which have already been taken in an administration cycle, a symbol for confirming that a medicament portion has been taken, and also a symbol as a warning indicator that an interruption phase must not be initiated if the user attempts to initiate an interruption phase. These symbols can each be represented as a continuous display or in the form of a flashing display. The symbols are preferably displayed on the display device as alternatives or, sometimes, at the same time. In addition, the display device can be designed in such a way that further warning signals which can be optically, acoustically and/or haptically perceived can be emitted.

The display device comprises an electronic actuation means for the display. This may be, in the conventional manner, a programmed or programmable microprocessor circuit.

The display device is preferably controlled by operator control elements on the dispenser. These operator control elements may be, in particular, buttons or other sensors. By way of example, a menu button and a confirmation button can be provided. The menu button serves to select specific display or selection modes. The confirmation button serves to make a possible selection in a specific mode.

The dispenser can comprise, in addition to the display, further optical indicator elements such as LEDs and additionally acoustic alarm devices (loudspeakers) and/or mechanical alarm devices (vibrators).

All the indicator elements of the display device can either be displayed in a continuous manner or be displayed in a flashing manner. In addition, the indicator elements can also be displayed in a neutral (if possible contrasting) colour, for example in black, or all or else only individual indicator elements can be in a signal colour, for example in red. In order to emphasize the importance of the display of specific operator control states in the dispenser and in the display device, escalation stages can be provided, for example a coloured, for example red, representation can be provided instead of a black representation. As an alternative or cumulatively, a flashing display can be selected instead of a continuous display.

It is particularly preferred if the display device is combined with a dispenser for the medicament portions. In this case, the dispenser can trigger the display device in the event of removal of a medicament portion without a user acting as an intermediary, that is to say removal of a medicament portion leads immediately to removal of a medicament portion being taken into account without the user additionally having to perform a separate input operation for the removal. This triggering can be performed mechanically, electromechanically, electronically or in some other way. In particular, the dispenser can permit output of medicament portions based on the mechanical or electromechanical transmission of force from operating means to an output unit, and provision may also be made for the mechanical or electromechanical transmission of force to act directly on the display device in the event of a medicament portion being removed, for example by means of a switch, so that the removal is thereby registered in the display device without additional manipulation by the user. Automatic triggering largely prevents incorrect operator control by it being impossible for the user to falsely log removal in the display device.

The medicament portions can be prepared, as in conventional dispensers, in the form of tablets, pills, coated tablets or the like. The portions can, in principle, be packaged in the form of blisters. The medicament portions are preferably packaged in cartridges, that is to say in a column-like arrangement. In this case, the medicament portions can be output through an axial opening in the cartridge.

The present invention will be illustrated in greater detail with reference to the figures described below. The embodiments shown in the said figures and the description of the figures serve only to illustrate, and not to restrict, the invention.

FIG. 8a shows the display of the display device according to the invention in the first embodiment according to the invention after the first reference administration time is exceeded and additionally with changeover (switch on/switch off) of the acoustic warning function;

FIG. 9 shows the display of the display device according to the invention in the first embodiment according to the invention when a transition is made to the interruption phase;

FIG. 11a shows the display of the display device according to the invention in the first embodiment according to the invention before and after removal of two tablets, without taking into account the second tablet for the administration after the first reference administration time is exceeded by a short time;

FIG. 11b shows the display of the display device according to the invention in the first embodiment according to the invention before and after removal of two tablets, without taking into account the second tablet for the administration after the first reference administration time is exceeded by a longer time;

FIG. 12a shows the display of the display device according to the invention in the first embodiment according to the invention before and after removal of two tablets, also taking into account the second tablet for the administration after the first reference administration time is exceeded by a short time;

FIG. 12b shows the display of the display device according to the invention in the first embodiment according to the invention before and after removal of two tablets, also taking into account the second tablet for the administration after the first reference administration time is exceeded by a longer time;

FIG. 22 shows examples of administration and missed administration (=no administration) of tablets within an administration regime for contraception.

Identical elements are provided with the same reference symbols. Where tablets are mentioned in the text which follows, this is done as a simplification of the term medicament portions. This term is therefore likewise intended to include pills, coated tablets, capsules and other portioned solid administration forms. In the following, the display device is shown and described for use for medicament portions which are contraceptives and which are taken in a flexible administration regime, that is to say with a compulsory administration phase of 24 days, followed by a flexible administration phase of up to a further 96 days (a maximum of 120 days in total), and a subsequent interruption phase of 4 days.

Figure 1:
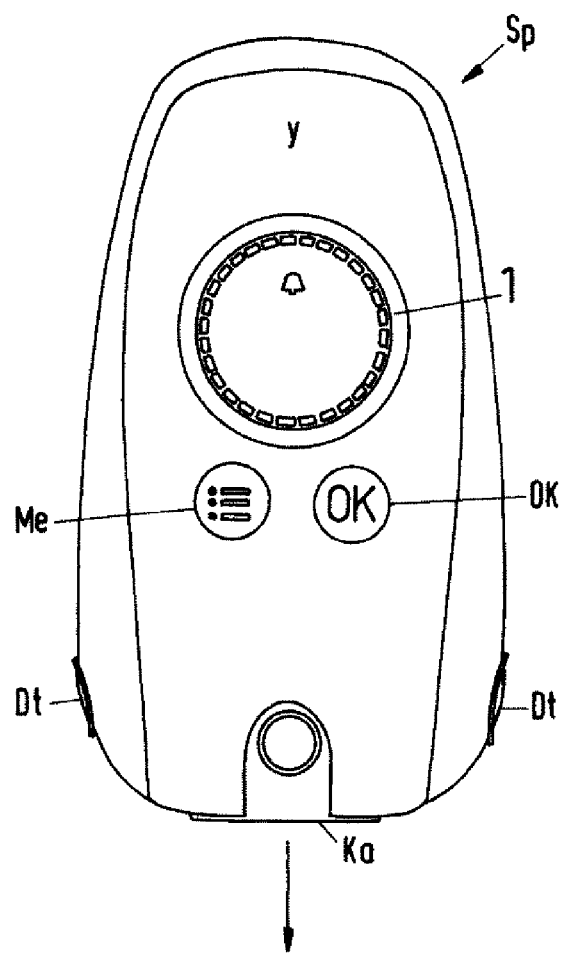
FIG. 1 shows a front view of a dispenser having a display device according to the invention.

FIG. 1 shows a front view of a dispenser Sp for medicaments. The lower part of a medicament cartridge Ka, which is inserted into the dispenser axially from below, can be seen in the lower region of the dispenser. The medicament portions are output from the bottom (arrow). To this end, the cartridge has, on the lower face, an ejector mechanism which is operated by means of lateral pushbuttons Dt.

A display device with a display 1 and operator control buttons Me, Ok is also fitted on the front face of the dispenser Sp. The menu key Me serves to select a specific display or selection mode on the display, and the confirmation key Ok serves to confirm the selection of a function which is displayed by the display.

Figure 2:
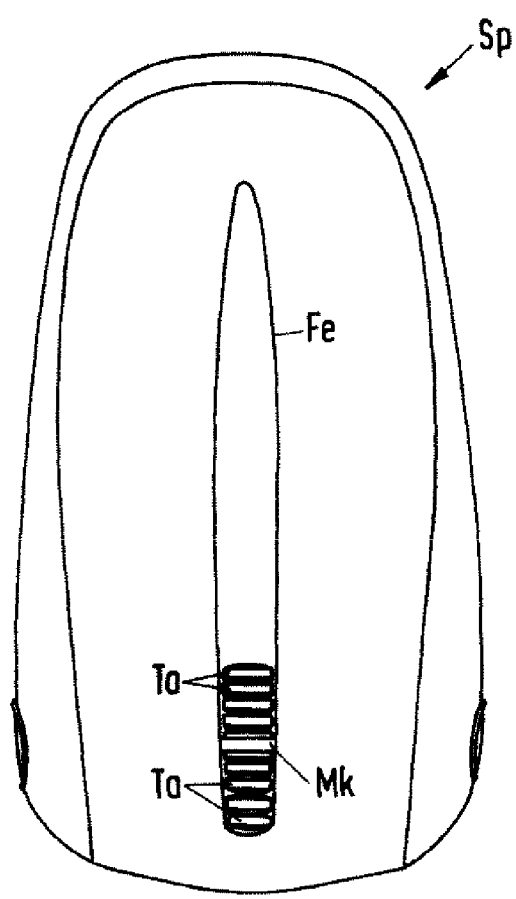
FIG. 2 shows a rear view of the dispenser.

FIG. 2 shows a rear view of the dispenser Sp. The housing of the dispenser Sp is provided, in the centre and axially, with a window Fe on the rear face, some of the tablets Ta which are contained in the cartridge being visible through the said window. A marker Mk in the form of a line is also provided, this marker indicating the filling level at which the cartridge contains just 7 tablets. Therefore, the user can also directly optically monitor the filling level of tablets in the dispenser.

Figure 3:
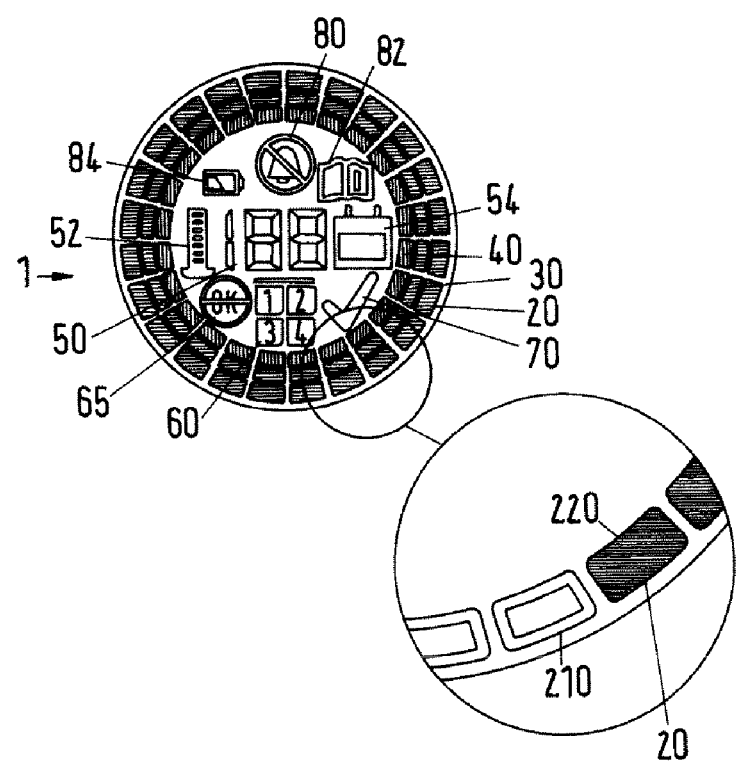
FIG. 3 shows a plan view of the display of the display device according to the invention in a first embodiment according to the invention.

FIG. 3 shows the display 1 of a display device according to the invention with an enlarged illustration of a detail of indicator elements 20 which are located in a ring. This illustration serves only to show all the possible indicator elements and symbols on the display. All elements and symbols are usually not visible at the same time but only displayed in accordance with the display situation.

The display is preferably an LCD display which particularly preferably has a lighting means or at least optionally has a lighting means. The indicator elements and symbols illustrated here do not need to be continuously displayed either. During an inoperative period, that is to say during a phase in which the user is not operating the dispenser and the display device is not activated by any buttons being pushed, the display device can be automatically switched over to an inoperative position in which the indicator elements and symbols are not visible. The display device can be switched back to an active state by, for example, a button being pushed.

Most of the indicator elements and symbols of the display 1 are, for example, coloured black in order to provide a good contrast with the background. However, some indicator elements and symbols can be differently coloured.

The display 1 is equipped with sectoral indicator elements 20, 30, 40 which are in each case located in a ring. These rings are arranged concentrically to one another. The second indicator elements 20 in the outer ring make up, when taken together, the second visualization means. 24 such sectoral second indicator elements form a ring. In the case of the present exemplary embodiment, the 24 second indicator elements are each intended to represent 1 hour, and therefore all 24 second indicator elements symbolize 24 hours, that is to say 1 day. In order to illustrate where the second indicator elements are located, indicator frames 210 are provided, these indicator frames also being visible when the indicator zones 220 of the second indicator elements which are arranged in these frames are not displayed. The first indicator elements 30 and 40 make up, when taken together, the first visualization means. Whereas the first indicator elements 30 are coloured black, the first indicator elements 40 can be coloured red. In each case 24 such sectoral second indicator elements form a ring, with two rings of second indicator elements being provided. The first black-coloured indicator elements 30 are arranged in a first zone (central ring) and the first red-coloured indicator elements 40 are arranged in a second zone (inner ring). The second zone serves to show that a predefined third period of time has been exceeded, with the third period of time being represented by all of the first indicator elements 30 in the entire central ring. After the time at which all the second indicator elements 30 are completely displayed in the central ring is exceeded, the second indicator elements 40 are successively displayed in the inner ring in accordance with the progression of time.

There is also a three-digit digital display 50 in the centre of the display 1, the said digital display having different meanings depending on mode. A symbol 52 for a cartridge is shown on the left of the digital display. When this symbol and the digital display are displayed at the same time, the digital display is displaying the number of tablets still in the cartridge. This symbol can be displayed both as a continuous display and in a flashing manner, the latter being the case when there are no more tablets in the cartridge. In addition, a symbol 54 for a calender is shown on the right of the digital display. When this symbol and the digital display are displayed at the same time, the digital display displays the number of days which have elapsed in the current administration cycle.

Furthermore, a symbol 60 for an interruption in administration is located beneath the digital display 50. When this symbol appears together with the digital display, the digital display is displaying the number of days which have already elapsed in the interruption phase.

Furthermore, a warning and information symbol 65 which is displayed in various situations, specifically in a continuous display or in flashing manner, is located on the left of the symbol 60 for an interruption in administration. The said warning and information symbol can, in the display shown here, be shown having been struck-through and also without having been struck-through. When displayed having been struck-through, this symbol is displayed together with the symbol for the interruption phase and then indicates that an interruption phase must not be initiated (yet).

Furthermore, a confirmation symbol 70 which appears, for example, when removal of a tablet is confirmed as having been administered is located on the right of the symbol 60 for the interruption in administration.

An information symbol 80 for displaying that an acoustic warning indicator is activated (without having been struck-through) or deactivated (having been struck-through, as illustrated in the figure) is located above the digital display 50. An alarm symbol 82 as a prompt to the user to consult the operating instructions is shown at the top-right, and a warning symbol 84 about a low battery charge state is shown at the left. These two symbols are not coloured black but preferably red or another signal colour in order to emphasize the warning characteristics of these displays. In addition, the alarm symbol 82 can be produced not only with a continuous display but also as a flashing display, the latter being the case when the user attempts to initiate the interruption phase during the compulsory administration phase.

Figure 4:
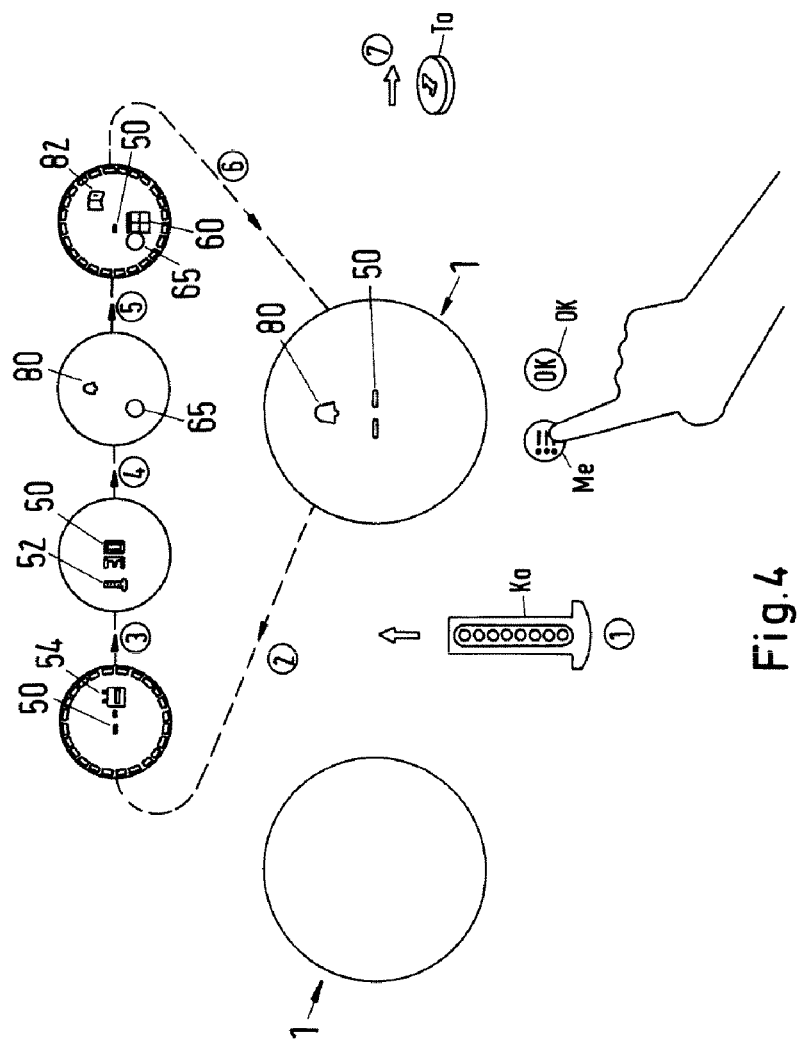
FIG. 4 shows the display of the display device according to the invention in the first embodiment according to the invention before a cartridge is first inserted and then in different display modes.

FIG. 4 shows the display 1 of the display device according to the invention, in the first instance before the cartridge which is filled with tablets is first inserted into the dispenser, and then after the said cartridge has been inserted.

Before a cartridge is inserted into a dispenser for the first time, no indicator elements or symbols are visible on the display 1 (illustration on the left) because, in this case, the dispenser is designed such that the battery in the dispenser is not yet connected to the display device. The cartridge Ka is then inserted into the dispenser (step 1). As a result, the dispenser and the display device are activated. The start-up display appears on the display 1 (default screen). Initially, only the acoustic information indicator 80 and, representing a digital numerical display by the digital display 50, two horizontal dashes are produced on the display as standard. This illustration is the standard display of the display.

The available modes are displayed next to one another in the display 1 by the menu key Me now being confirmed once or more than once:

After the menu key Me is pushed once (step 2), the first display mode appears in a first level, the days which have already passed in an administration cycle being displayed in the said first display mode: The calender symbol 54 is displayed next to the two dashes of the digital display 50 which are still displayed as standard at this stage. This is intended to symbolize, in this stage before a tablet is first removed from the dispenser, that a value for the number of days which have elapsed in an administration cycle cannot be displayed yet.

After the menu key Me is pushed twice (step 3) the second display mode appears in a second level, the number of tablets still contained in the cartridge being displayed in the said second display mode: The cartridge symbol 52 appears next to the digital display 50. This cartridge symbol is intended to indicate that 30 tablets are contained in the inserted cartridge in the present case. The cartridge symbol is produced with a continuous display—not in a flashing manner. The cartridge symbol flashes only when the number of tablets falls below, for example, 6 (preset value). In this case, the cartridge symbol, which is intended to indicate that there are only a few tablets remaining in the cartridge, will also be hidden on the default screen.

After the menu key Me is pushed three times (step 4), the third display mode appears in a third level, it being possible for the acoustic alarm mode to be switched on or switched off in the said third display mode. In addition to the display of the acoustic information display 80, the warning/information symbol 65, which flashes, is also shown.

After the menu key Me is pushed four times (step 5), the fourth display mode appears in a fourth level, the interruption phase being initiated or displayed in the said fourth display mode: The symbol 60 for the interruption in administration is displayed at the bottom-centre of the display 1. The digital display 50 is located in the centre and, in the present case, shows a single horizontal dash instead of a single-digit number for the number of interruption stages. The alarm symbol 82 is shown at the top-right and the warning/information symbol 65 and a struck-through OK display are shown at the bottom-left since, in the present phase, the user is still at the beginning of the administration phase and therefore cannot yet initiate the interruption phase.

The last-mentioned two levels (third and fourth levels) can also be interchanged.

After the menu key Me is operated once again (step 6), the display device returns to the mode with the standard display. The display device would similarly automatically return from one of the first to fourth display modes to the mode of the standard setting if the menu key is not operated for a period of 3 seconds.

Figure 5:
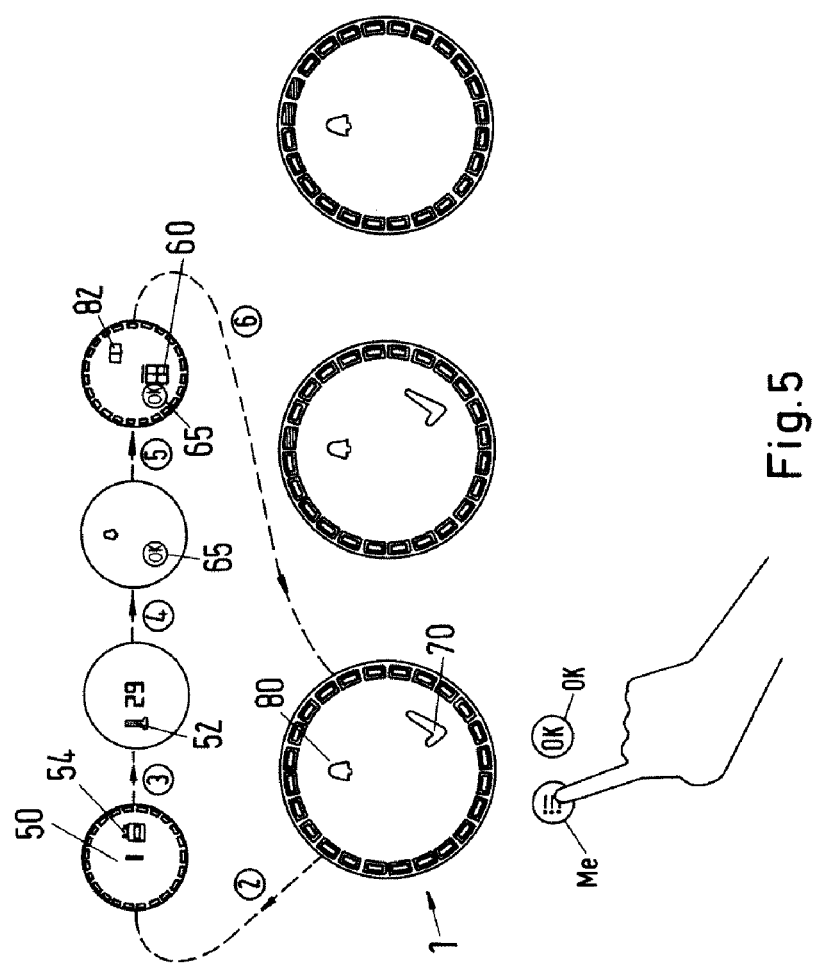
FIG. 5 shows the display of the display device according to the invention in the first embodiment according to the invention after a tablet is first removed in an administration cycle.

The user can now remove a tablet Ta from the dispenser (step 7). The administration regime is started by the tablet being removed. In particular, the second visualization means is started first:

FIG. 5 shows the display 1 of the display device after the first tablet has been removed. If the tablet had been removed, for example, at 7:00, this time represents the second reference administration time. A ring of 24 indicator frames 210 of the second visualization means, which indicator frames each symbolize 1 hour, appears on the display. As can be seen at the bottom-left of the illustration, none of the indicator frames 210 is yet filled with an indicator zone immediately after the first tablet is removed. Furthermore, the display device shows the confirmation symbol 70 and the information symbol 80 for the acoustic warning indicator. The confirmation symbol indicates that a tablet has been successfully removed for administration.

The following displays are shown in the first to fourth display modes after repeated operation of the menu key Me:

After the menu key is operated once (step 2), the first display mode appears, this display mode indicating that 1 day has passed in the current administration cycle. After the menu key is operated twice (step 3), the second display mode appears, this display mode displaying that there are still 29 tablets in the cartridge. After the menu key is operated three times (step 4), the third display mode appears, it being possible for the acoustic alarm mode to be switched on or switched off in this display mode. After the menu key is operated four times (step 5), the fourth display mode appears, the interruption phase being initiated or displayed in this display mode.

However, this is not possible in the current phase since the user is still in the compulsory administration phase (warning/information symbol 65 struck-through) after the administration of just 1 tablet.

After the menu key Me is operated once again (step 6), the display 1 returns to the mode with the standard display. As time progresses, the two following displays appear after the first tablet has been removed and administered: The bottom-centre illustration shows that approximately 1 hour has passed since removal (first indicator frame 210 of the second visualization means filled with an indicator zone). The bottom-right illustration shows that approximately 2 hours have passed since removal (two indicator frames 210 filled with indicator zones).

Figure 6:
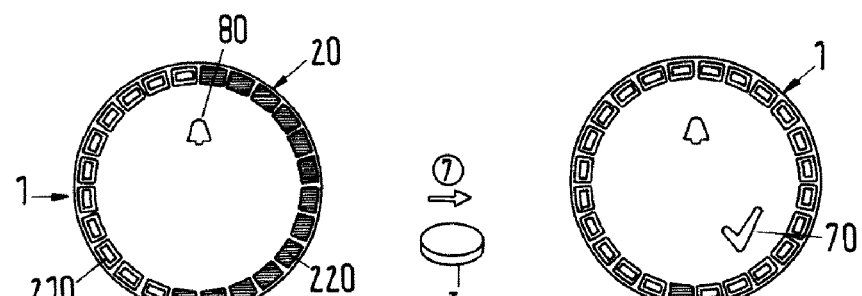
FIG. 6 shows the display of the display device according to the invention in the first embodiment according to the invention before and after removal of a tablet before the second reference administration time elapses.

The further progression of time is shown, by way of example, in FIG. 6 in the standard display. In the left-hand illustration of the display 1, approximately 13 hours have passed since the last second reference administration time.

The tablet does not necessarily have to be taken at the reference administration time. It suffices for the said tablet to be taken within an administration time interval. In the present case, the said tablet can be taken, for example, within a time interval of 12 hours before, to 2 hours after, the reference administration time. In the present case, the tablet Ta is taken within the administration time interval of 12 hours before the reference administration time (step 7). Therefore, the confirmation symbol 70 appears in the display 1 which appears in response. At the same time, the remaining time until the next reference administration time is illustrated in the sense of a "negative time" since the indicator frame 210 is first filled with indicator zones which lie in the ring which extends from the time of removal and administration (−11 hours) to the current second reference administration time. The indicator frames are then again filled with indicator zones in the normal manner, starting from the first indicator element at the top.

Figure 7:
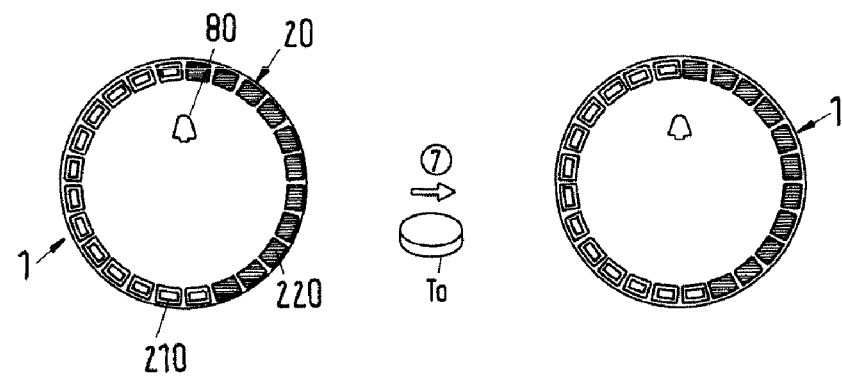
FIG. 7 shows the display of the display device according to the invention in the first embodiment according to the invention before and after removal of a tablet before the beginning of the administration time interval.

A different procedure is followed if the tablet Ta has already been removed from the dispenser prematurely, that is to say before the beginning of the administration time interval. This is shown by way of example in FIG. 7. In this case, the second period of time since the last second reference administration time is only 11 hours. Therefore, subsequent removal of a tablet Ta (step 7) is not logged as effective administration (the confirmation symbol is not displayed, there is no change in the display of the second visualization means).

FIG. 8a shows the display 1 of the display device after the first reference administration time is exceeded (illustration at the bottom-left). In this case, both the second indicator elements 20 of the second visualization means, which second indicator elements are all displayed, and also the 5 first indicator elements 30, which symbolize that the user has not taken any tablets after a first period of time which exceeds the first reference administration time by 5 hours has elapsed, are shown in the outer ring. After repeated operation of the menu key Me, the user successively arrives at the first display mode which shows that the user is on the 28th day of the administration cycle (step 2), at the second display mode which shows that there are still 18 tablets in the cartridge (step 3), and at the third display mode in which there is an option to switch on or switch off the acoustic information indicator 80 (step 4). In the present case, the information indicator is switched on since the information symbol 80 is not struck-through. The state "acoustic warning indicator off" is selected (step 10) by operating the confirmation key Ok. This selection can be cancelled by pushing the said key again. It is possible to switch between these two states as often as desired.

In addition, the warning/information symbol 65 is shown in the flashing state in the present case. This means that the user can change over to the interruption phase in this administration phase (flexible administration phase).

Figure 8B:
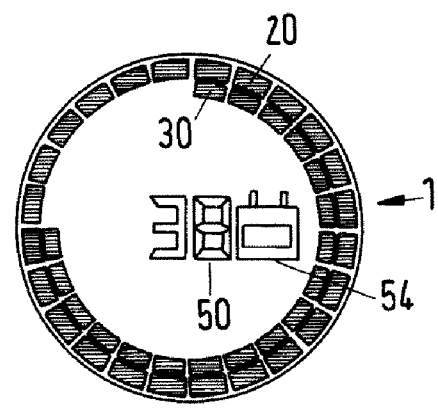
FIGS. 8b, 8c show the display of the display device according to the invention in the first embodiment according to the invention after the first reference administration time is exceeded given different first periods of time.
Figure 8C:
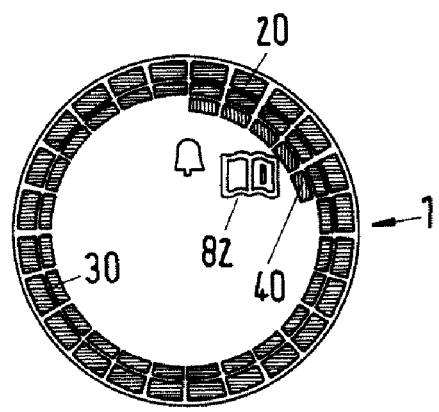

Further illustrations of a first reference administration time being exceeded are shown in FIGS. 8b and 8c: FIG. 8b shows an overrun by 18 hours (second indicator elements 20 are all present and 18 first indicator elements 30 are present) and FIG. 8c shows an overrun by 29 hours (second indicator elements 20 are all present, first indicator elements 30 are all present and 5 first indicator elements 40 are present). The display in FIG. 8b also indicates that the user is on the 38th day of the administration cycle, that is to say is in the flexible administration phase. In the case of FIG. 8c, the user is also advised to consult the operating instructions (alarm symbol 82) because of the first reference administration time being considerably exceeded by 29 hours.

FIG. 9 shows the transition to the interruption phase:

The illustration of the display 1 at the bottom-left shows that the user has exceeded the first reference administration time by 5 hours. This can be identified by all the first indicator elements 20 of the first visualization means and 5 of the second indicator elements 30 of the second visualization means being displayed. By repeated operation of the menu key Me, the display device is switched through the first to third display modes (steps 2, 3, 4, 5) to the fourth display mode. The symbol for the interruption in administration 60, the warning/information symbol 65 and the digital display 50 are displayed in this display mode. The warning/information symbol indicates that it is possible to initiate an interruption phase. This is the case because the user is on the 28th day of the administration cycle (see display of the first display mode). The interruption phase is initiated by operating the confirmation key Ok (step 9). The digital display 50 on the display 1 then indicates that the user is on the first day of the interruption phase.

Figure 10:
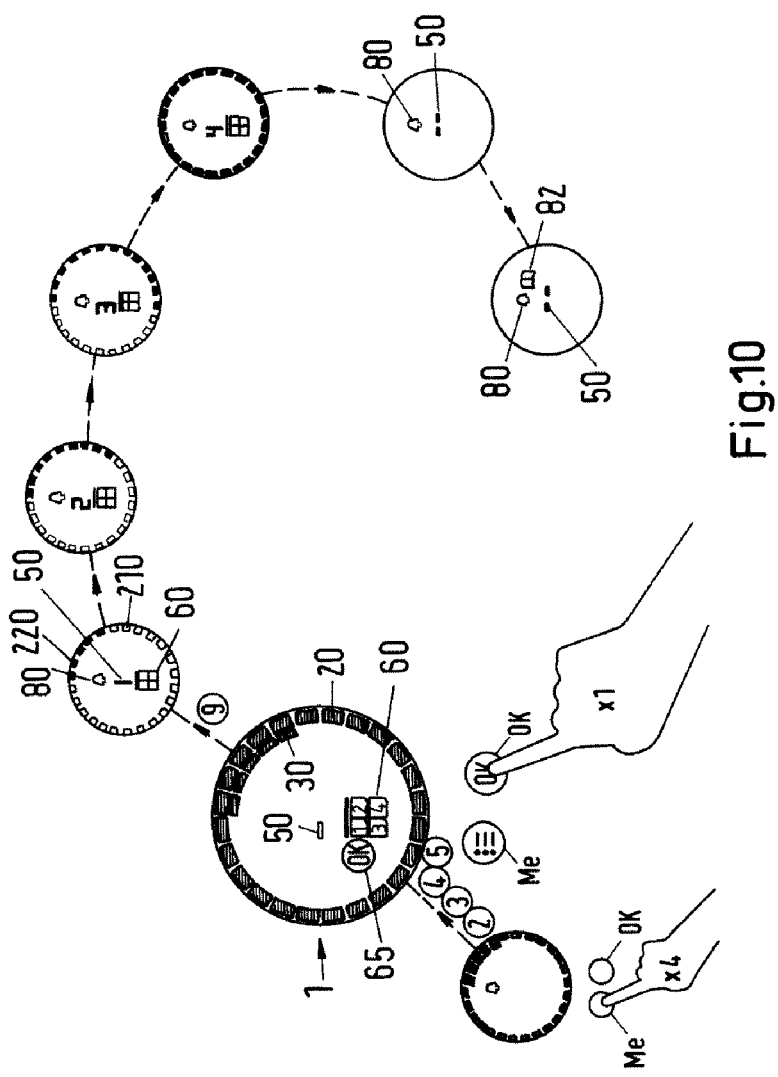
FIG. 10 shows the display of the display device according to the invention in the first embodiment according to the invention during the interruption phase.

The following displays can be seen successively in the display 1 in the interruption phase (FIG. 10):

Proceeding from the administration phase in which the display 1, which is illustrated on a small scale at the bottom-left, is shown with the standard display, the fourth display mode is selected by operating the menu key Me (steps 2, 3, 4, 5). The display in which the user has the choice to initiate the interruption phase appears. This is indicated by the symbol 60 for the interruption in administration. The warning/information symbol 65 also confirms that it is possible to start the interruption phase. In addition, the indicator elements 20 of the second visualization means indicate that 5 hours have passed on this first day. This period is the period which has passed since the first reference administration time (see time display of the second visualization means on the display according to the larger illustration of the display). A changeover is made to the interruption phase by operating the confirmation key Ok (step 9). The digital display 50 now indicates that the user is on the first day of the interruption phase.

The user does not take any tablets during the interruption phase. The display 1 shows, by way of the digital display 50 and the second indicator elements 20 of the second visualization means, the period which has respectively elapsed. In the illustrations shown here, 5 hours have passed since the reference administration time on the first day (that is to say a total of 5 hours), 9 hours have passed since the reference administration time on the second day (that is to say a total of 33 hours), 13 hours have passed since the reference administration time on the third day (that is to say a total of 61 hours) and 23 hours have passed since the reference administration time on the fourth day (that is to say a total of 95 hours). The display then immediately switches to the start-up display. If a new tablet is taken in this situation, the result is the sequence which has already been described with reference to FIGS. 4, 5. If, in contrast, a tablet is not taken, the alarm symbol 82 appears permanently (last illustration in the series of illustrations in FIG. 10). The user is thus advised to consult the operating instructions. An acoustic signal can also sound in order to remind the user to start the new administration phase, for example for a few seconds, with the acoustic signal being repeated several times in a specific rhythm, for example at intervals of 15 minutes.

When several tablets are removed shortly one after the other, the second removal operation is not taken into account as administration (FIG. 11):

If, for example, a first tablet Ta is taken when the first reference administration time is exceeded by 7 hours (FIG. 11a: left-hand illustration: second indicator elements 20 (outer ring) are all present and 7 first indicator elements 30 (inner ring) are present) (step 7), the device changes over to a display according to which 7 hours have passed since the last second reference administration time (FIG. 11a: central illustration: 7 second indicator elements 20 are all present). In this case, the removal is confirmed by the confirmation symbol 70. However, when another tablet Ta is removed, this is no longer taken into account as administration (FIG. 11a: right-hand illustration: no further change in the indicator elements 20, the confirmation symbol is not displayed).

In another configuration, 30 hours have passed since the first reference administration time (FIG. 11b: left-hand illustration: second indicator elements 20 (outer ring) are all present, first indicator elements 30 (central ring) are all present and 6 first indicator elements 40 (inner ring) are present). In this case, the alarm symbol 82 is hidden on account of the first reference administration time being exceeded to a considerable extent. When a tablet Ta is removed (step 7), the device changes over to a display according to which 6 hours have passed since the last second reference administration time (FIG. 11b: central illustration: 6 second indicator elements 20 are all present). The removal is confirmed by the confirmation symbol 70. However, in this situation, the user is advised to consult the operating instructions (alarm symbol 82 is displayed). However, when another tablet Ta is taken, this is no longer taken into account as administration (FIG. 11b: right-hand illustration: no further change in the indicator elements 20, no confirmation symbol).

When several tablets are removed, these tablets being assigned to different reference administration times, second removal of a tablet is taken into account as administration (FIG. 12):

If, for example, a first tablet Ta is taken when the first reference administration time is exceeded by 15 hours (FIG. 12a: left-hand illustration: second indicator elements 20 are all present and 15 first indicator elements 30 are present) (step 7), the device changes over to a display according to which 15 hours have passed since the last second reference administration time (FIG. 12a: central illustration: 15 second indicator elements 20 are all present). The removal is confirmed by the confirmation symbol 70. When another tablet Ta is removed, this is taken into account as further administration because this second removal takes place within the time interval of the next reference administration time (time interval begins at the reference administration time minus 9 hours). This administration is again confirmed by the confirmation symbol 70. In addition, the display 1 now shows first a new negative second period of time: FIG. 12a, right-hand illustration, shows that the second indicator elements 20 start to count starting from an indicator element 20 "reference administration time minus 9 hours".

In another configuration, 42 hours have passed since the first reference administration time (FIG. 12b: left-hand illustration: second indicator elements 20 are all present, first indicator elements 30 are all present and 18 first indicator elements 40 are present). In this case, the alarm symbol 82 is hidden on account of the first reference administration time being exceeded to a considerable extent. When a tablet Ta is removed (step 7), the device changes over to a display according to which 18 hours have passed since the last second reference administration time (FIG. 12b: central illustration: 18 second indicator elements 20 are all present). The removal is confirmed by the confirmation symbol 70. However, here too, the user is advised to consult the operating instructions because of the first reference administration time being exceeded to a considerable extent (alarm symbol 82 is displayed). However, when another tablet Ta is taken, this is taken into account as further administration because this second removal takes place within the time interval of the next reference administration time (time interval begins at reference administration time minus 12 hours). This administration is again confirmed by the confirmation symbol 70. In addition, the device now first shows a new negative second second period of time: FIG. 12a, right-hand illustration, shows that the second indicator elements start to count starting from an indicator element 20 "reference administration time minus 6 hours".

Figure 13:
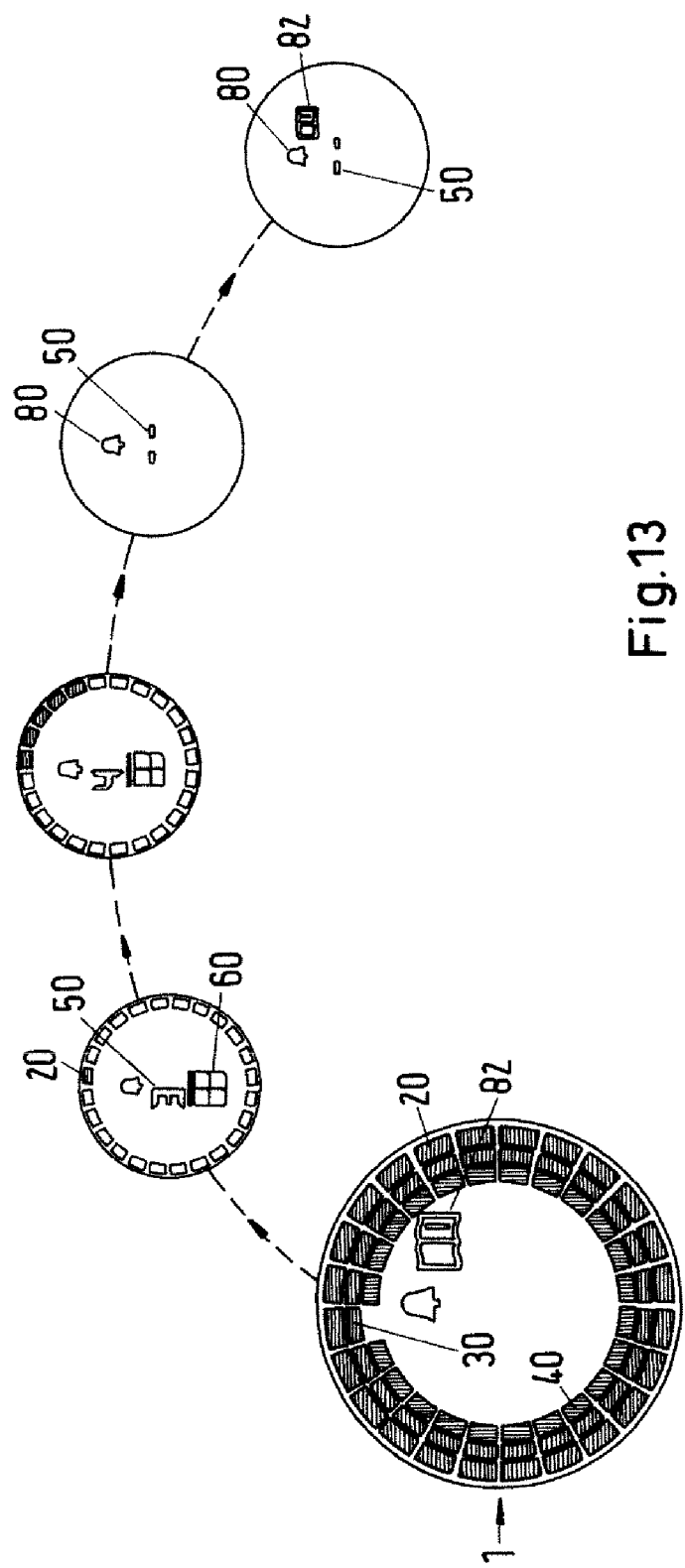
FIG. 13 shows the display of the display device according to the invention in the first embodiment according to the invention in the event of an automatic transition from the flexible phase to the interruption phase.

If the user fails to take the tablets over a longer period of time, the display device automatically starts the interruption phase. FIG. 13 shows how the device automatically changes over from the flexible phase to the interruption phase:

Proceeding from a display according to which the first reference administration time has already passed 47 hours before (large left-hand illustration: second indicator elements 20 are all present, first indicator elements 30 are all present and 23 first indicator elements 40 are present) and the user is prompted by the alarm symbol 82 to consult the operating instructions, the device automatically changes over to the (smaller) display 1 illustrated to the right of the said first illustration 2 hours later, after which the user is now in the interruption phase. This can be seen by virtue of the symbol 60 for the interruption in administration and that the digital display 50 has only one digit. The digital display indicates that the user is already on the third day of the interruption phase. This is the result of the relatively long time delay in removing tablets of, by now, over 48 hours. The further illustrations in FIG. 13 respectively show the situations on the fourth day of interruption (5 hours after the reference administration time), immediately after the end of the interruption period, and after a further time has passed without the user having removed a tablet.

Figure 14:
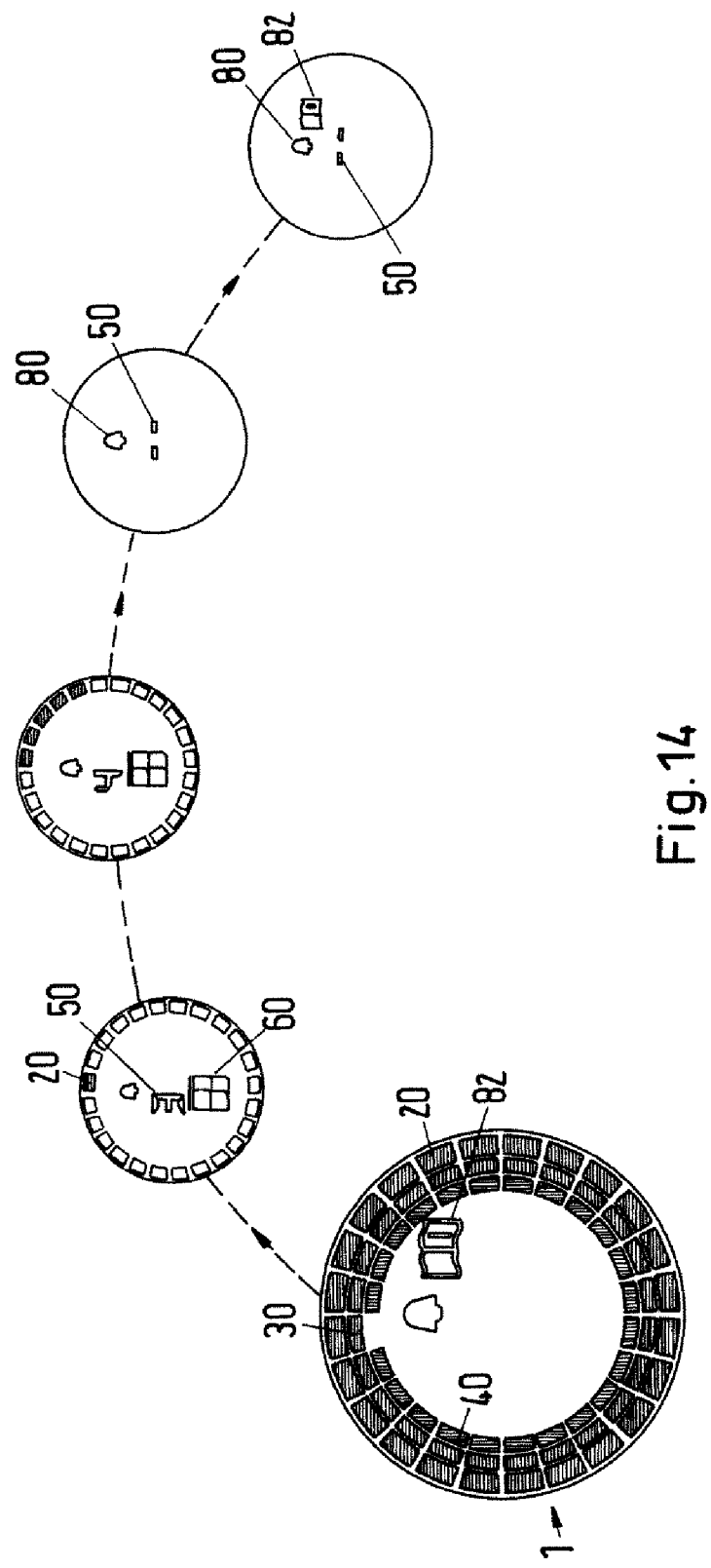
FIG. 14 shows the display of the display device according to the invention in the first embodiment according to the invention in the event of the automatic transition from the compulsory phase to the interruption phase.

FIG. 14 shows such a transition to the interruption phase in the case of the user failing to take the tablets in the compulsory administration phase too. Since contraception is not guaranteed in this situation on account of the tablet not being administered in any case, the display device changes over to the interruption phase in order to direct the user back to the administration phase. In this case, the display does not differ from that which appears when the changeover is made from the flexible phase to the interruption phase.

Figure 15:
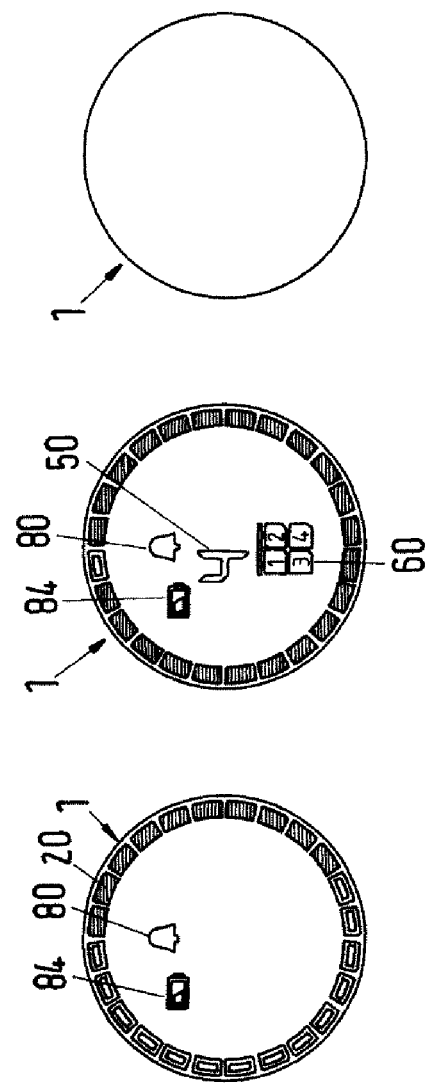
FIG. 15 shows the display of the display device according to the invention in the first embodiment according to the invention in the event of a low battery charge state.

FIG. 15 shows the display 1 with a low battery charge state. In the left-hand illustration of FIG. 15, the warning symbol 84 for a low battery charge state is shown. The display indicates that the user is in an administration phase (no symbol for the interruption phase). The charge state of the battery is always measured such that the administration cycle can still be maintained until the end. The user will therefore still be able to maintain the administration phase until the end of the interruption phase (central illustration). However, after the end of the interruption phase, the display device does not change over to the standard display but rather the display is switched off (right-hand illustration).

Figure 16:
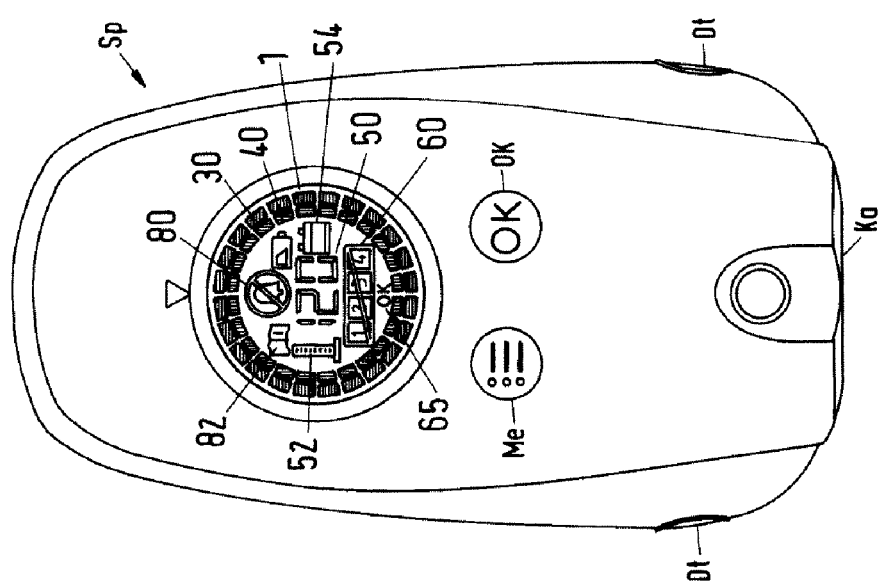
FIG. 16 shows the display of the display device according to the invention in a second embodiment according to the invention with alternative symbol representations.

FIG. 16 shows a second embodiment of a display of a display device according to the invention. Instead of the first sectoral indicator elements 30, 40 and the second sectoral indicator elements 20 in three rings, only sectoral first indicator elements, which are in two rings, can be seen here because both types of indicator elements do not appear at the same time in this embodiment. While the second indicator elements of the first type 30 are black, the second indicator elements of the second type 40 are coloured red in order to indicate a considerable time overrun to the user.

In addition, the design of the symbol 60 for interruption in administration, the warning and information symbol 65, the symbol 54 for the calender and the information symbol 80 for activation and deactivation of the warning indicator differ from the corresponding symbols of the first embodiment (see FIG. 3) in this case. A confirmation symbol is not provided. In addition, the arrangement of the symbols differs slightly from that of the first embodiment.

Figure 17:
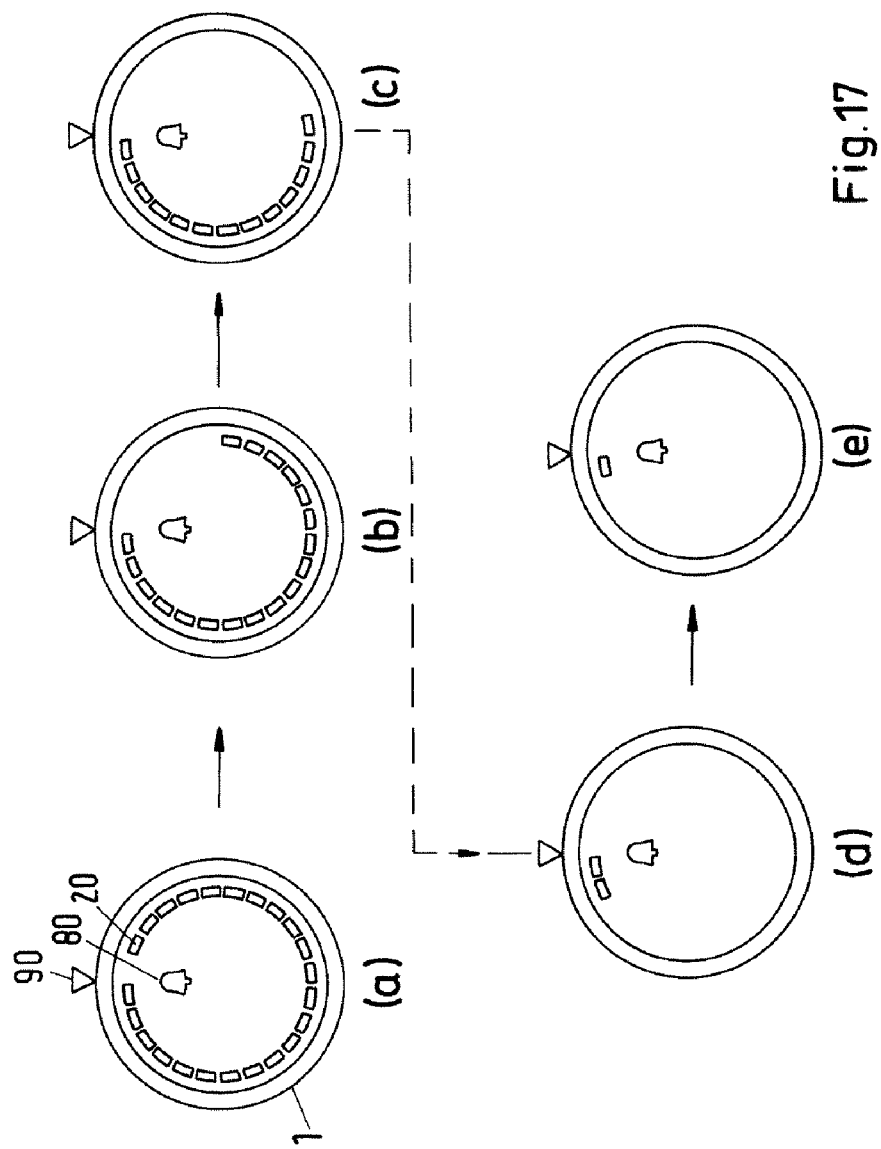
FIG. 17 shows the display of the display device according to the invention in the second embodiment according to the invention since the second reference administration time in various stages in the progression of time.

FIG. 17 shows the start-up display on the display 1 (default screen) in various stages over the progression of time: The second sectoral indicator elements 20, which indicate the progression of time since the second reference administration time (symbolized by the large external triangle 90), each represent 1 hour. Each of these indicator elements is made up of a substantially rectangular frame. Initially, all the indicator elements are switched on in order to indicate to a user that the entire period until the next reference administration time is still available. In the present case, 1 hour has already passed since the second reference administration time according to the illustration in FIG. 17(a). Since the last tablet was taken shortly before this display was recorded, the display already displays just 23 indicator elements in order to indicate that only 23 hours remain until the next reference administration time. When the next display (FIG. 17(b)) was recorded, 6 hours had already passed, and therefore 6 indicator elements are also switched off. Therefore, only 18 hours remain until the next reference administration time. FIGS. 17(c), (d) and (e) show corresponding illustrations 13 hours, 2 hours and, respectively, 1 hour before the next reference administration time.

If the next tablet is taken before the second reference administration time 90 is reached, an extended period of time remaining until the next second reference administration time for administration of the next tablet has to be displayed. This can be realized, for example, by all the second indicator elements 20 of the second visualization means and, furthermore, further indicator elements, which are, for example, in a ring, which is offset inwards in relation to the outer ring, and correspond to the residual period which exceeds 24 hours (not illustrated), being displayed after the removal of the tablet. If the next tablet is taken, for example, 2 hours before the second reference administration time (in accordance with FIG. 17(d)), all the indicator elements 20 would be displayed in the outer ring and, in addition, a further 2 indicator elements, which are located at the point of the indicator elements shown in FIG. 17(d) but offset inwards, would be displayed in a ring, which is situated further inwards, after the removal of the tablet. As time progresses further, only these two indicator elements would then first be successively cleared and only then will the first indicator elements be switched off one by one, starting with a first indicator element which is situated to the right of the marker 90 for the second reference administration time.

Figure 18:
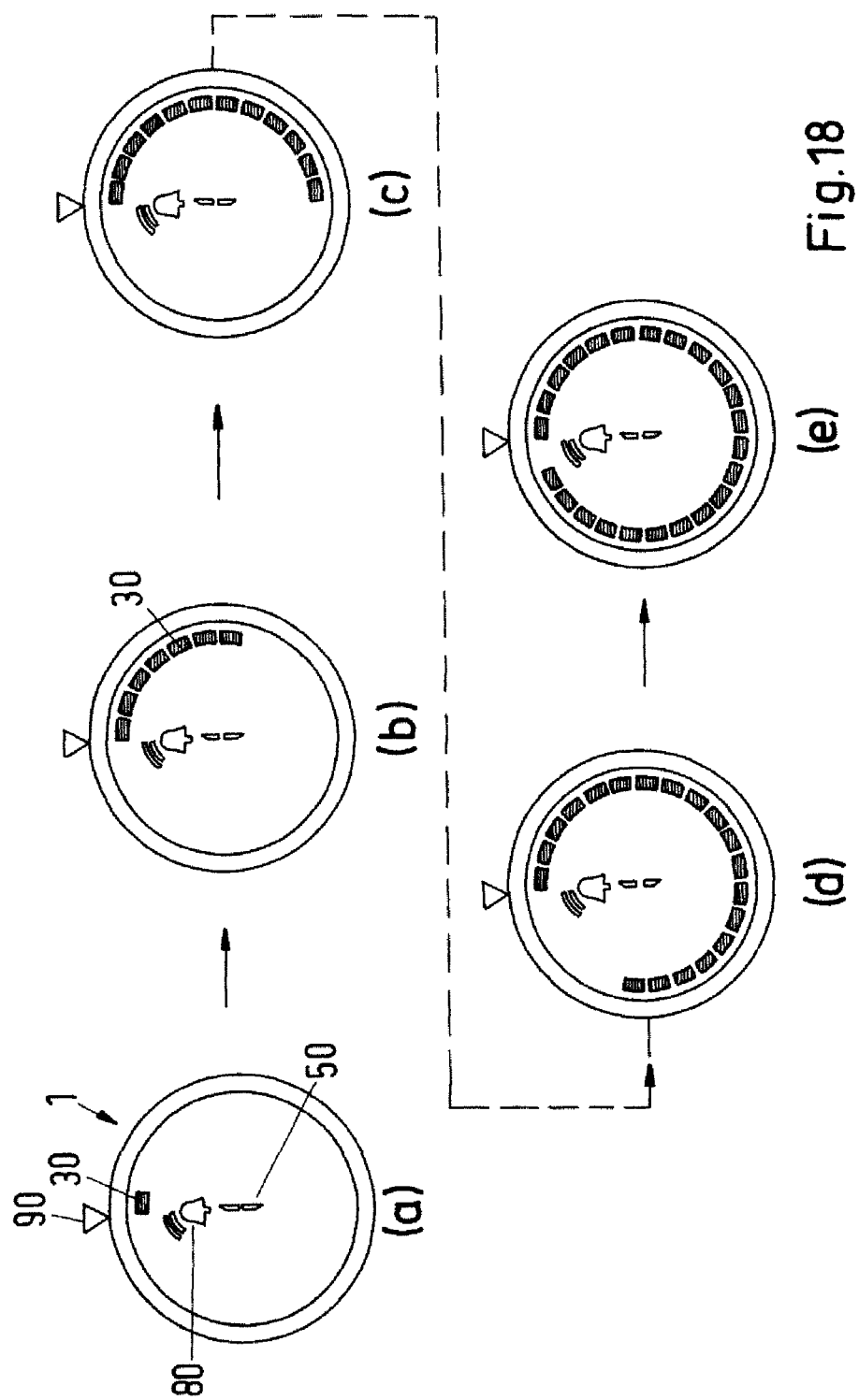
FIG. 18 shows the display of the display device according to the invention in the second embodiment according to the invention since the first reference administration time in various stages in the progression of time.

FIG. 18 again shows the start-up display on the display 1 (default screen) in various stages over the progression of time in accordance with FIG. 17, but in this case after the next reference administration time 90 has passed without a tablet having been taken. Therefore, the most recent reference administration time is a first reference administration time. After this reference administration time is reached without a tablet having been taken, the second indicator elements are cleared. After time progresses further after the first reference administration time, successive first indicator elements 30 which indicate the time overrun appear. FIG. 18(a) shows that 1 hour has passed since the first reference administration time. FIGS. 18(b)-(e) show further progressions in time, specifically 7 hours, 12 hours, 19 hours and, respectively, 23 hours since the first reference administration time. In addition, the numerical display 50 indicates that 1 tablet has not been taken by this point. Furthermore, the modified information symbol 80 for activating and deactivating the warning indicator (by the waves illustrated top-left) indicate that the administration time has been exceeded.

Figure 19:
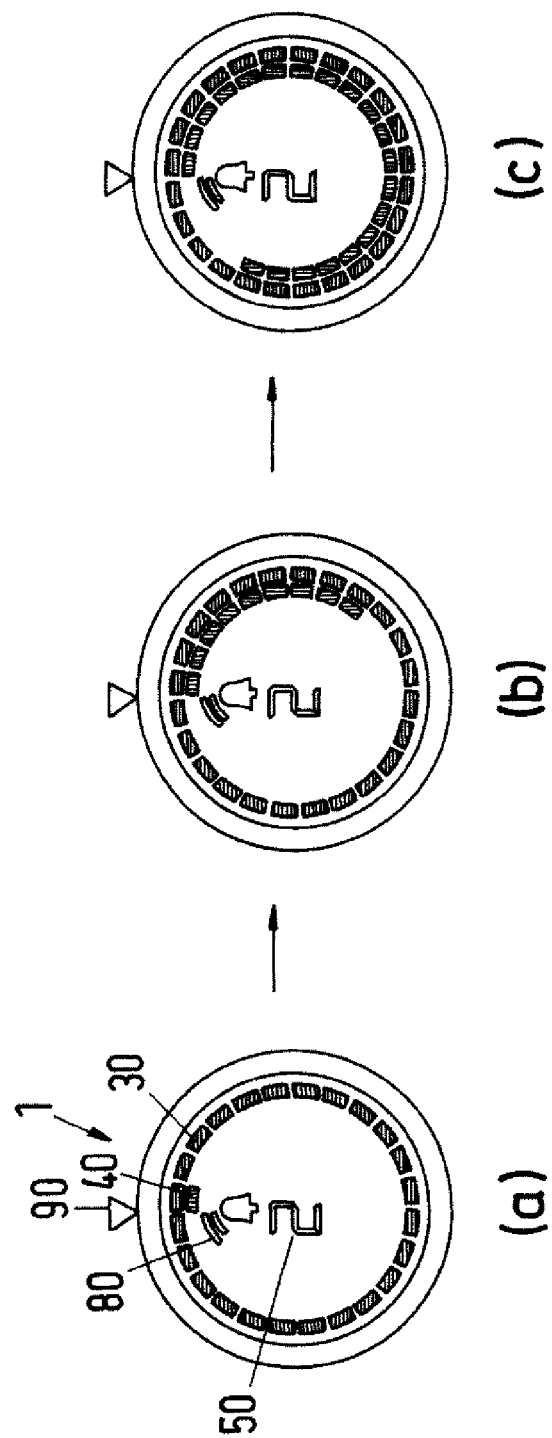
FIG. 19 shows the display of the display device according to the invention in the second embodiment according to the invention in the event of more than one administration period being exceeded in various stages in the progression of time.

FIG. 19 shows the further progression of time after more than 24 hours have elapsed since the first reference administration time. FIG. 19(a) shows the display which shows 24 hours +1 hour (=25 hours) since the first reference administration time. To this end, a further first indicator element 40 is now shown in a ring which is situated further inwards, in addition to the first indicator elements 30 in the outer ring. This further indicator element is preferably coloured red in order to warn the user of a further time overrun. Furthermore, the digital display 50 indicates that 2 tablets have now not been taken. In the further displays according to FIGS. 19(b) and 19(c), 24+9 hours (=33 hours) and, respectively, 24+20 hours (=44 hours) have passed since the first reference administration time.

Figure 20:
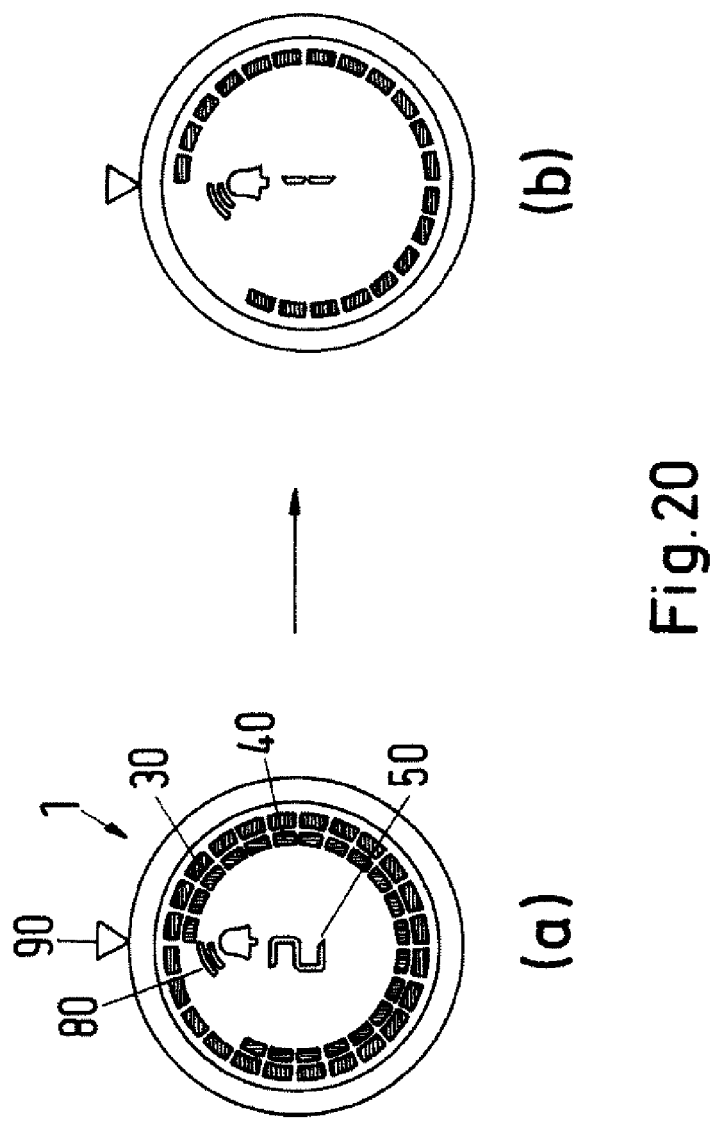
FIG. 20 shows the display of the display device according to the invention in the second embodiment according to the invention before and after removal of a tablet.

FIG. 20 shows the display 1 which is produced before (FIG. 20(a)) and after (FIG. 20(b)) a single tablet is removed. FIG. 20(a) corresponds to the illustration in FIG. 19(c). Before a tablet is removed, the display indicates that 2 tablets have not been taken. After the removal of 1 tablet, the display now shows that 1 tablet still has to be taken. This can be seen firstly on the digital display 50 and by the first indicator elements 40 being cleared and the first indicator elements 30 being partially cleared. It would now be necessary for 1 further tablet to be taken in order to again follow the required rhythm. If this further tablet is taken, the first indicator elements 30 are also cleared and (in the present case) another 4 second indicator elements are shown (not illustrated), these indicating the period until the next reference administration time.

Figure 21:
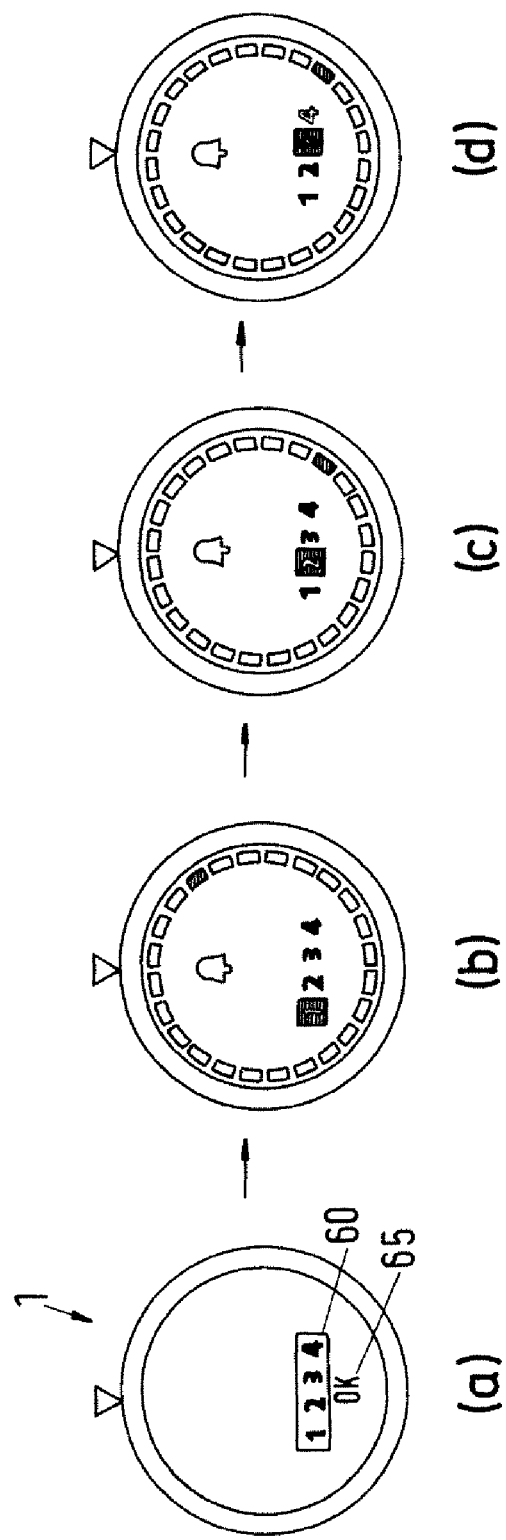
FIG. 21 shows the display of the display device according to the invention in the second embodiment according to the invention after an interruption phase is initiated.

FIG. 21 shows the display 1 which is produced after the interruption phase has been initiated. The symbol 60 for the interruption in administration and the warning and information symbol 65 appear in this case. Only these two symbols are displayed immediately after the interruption phase (FIG. 21(a)) is initiated. After run-in of a few hours after initiation, the display additionally shows that the user is on the 1st day of the interruption phase, specifically after 4 hours have elapsed (FIG. 21(b)). FIG. 21(c) shows the display which is produced on the 2nd day of the interruption phase, specifically after 24+9 hours (=33 hours) after the initiation. FIG. 21(d) shows the corresponding display on the 3rd day of the interruption phase after 24+24+9 hours (=57 hours) after the initiation.

Figure 22:
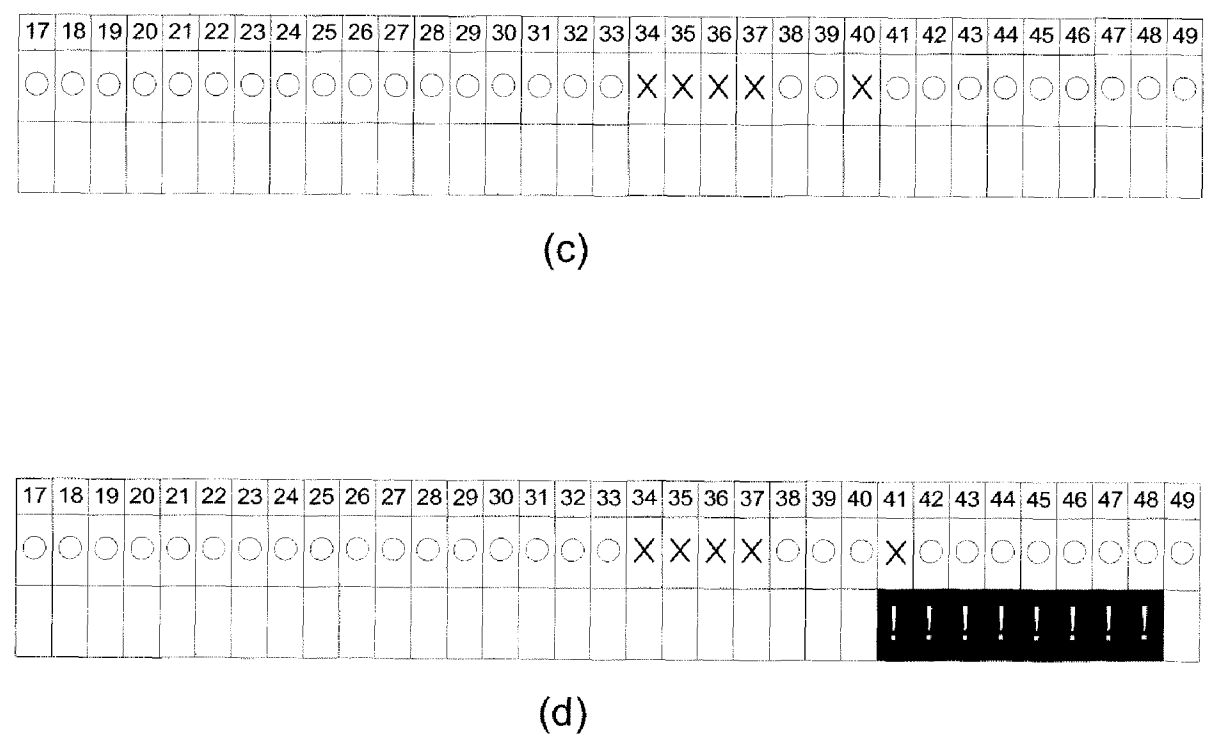

If the tablets for contraception are not taken regularly, contraception can no longer be ensured under certain conditions. In this case, it is necessary for the user to use additional contraceptives. This requirement can be displayed separately and specifically on the display 1 by means of a warning symbol for lack of contraception, for example by an exclamation mark ("!"). This warning symbol is only displayed if adequate contraception is no longer guaranteed, and is intended to indicate to the user that additional contraceptive means now need to be used. A situation such as this occurs if the tablets have not been taken regularly. This depends on the periods firstly for which tablets have been administered correctly, that is to say regularly, and secondly the periods for which tablets have been administered with an interruption. FIG. 22 shows examples of missed administration on specific days during the course of the administration regime (correct administration: "○", no administration "×") which, in two cases, leads to a state of lack of contraception. Therefore, additional contraceptive measures (need for additional use of other contraceptive means) are required in this case. To this end, the said warning symbol is displayed on the display:

The figures each show an excerpt from an administration calendar with the 17th, 18th, 19th days etc. in the administration regime being shown (day given in the first line). Administration of a tablet on the respective day is recorded in the second line by "○". If a tablet is not taken, an "×" is shown. The third line indicates whether additional contraceptive measures are required on the respective day ("!") or not (no entry in the associated field). In the first cases, this warning symbol appears on the display.

FIG. 22a shows an example of administration in which the administration of a tablet was forgotten on the 28th day and again on the 36th day. Additional contraceptive measures are not required (no entry in the third line) in this case for the following reasons: the tablet was not taken only on a single day within a period of 7 days of irregular administration (for example in the period of the 28th day to the 34th day) and this day was preceded by a 7-day period (21st day to 27th day) in which the tablets were taken regularly. Furthermore, the day on which the tablet was not taken, (28th day) is followed by a further 7-day period (29th day to 35th day) in which the tablets were taken regularly. In this case, the missed administration period is only 1 day (28th day). If the user again forgets to take the tablet at a later date (on the 36th day), this does not lead to additional contraceptive measures now having to be taken, for the abovementioned reasons. The period of 7 days between the two days of missed administration (28th day and 36th day) guarantees the ovulation-inhibiting action. For this reason, the warning symbol ("!") on the display is not activated either.

FIG. 22b shows an example for administration in which the tablets have not been taken on the 28th day and then again on the 34th, 35th, 36th and 37th days. Additional contraceptive measures are required in this case: Tablets have not been taken on two days, specifically on the 28th day and on the 34th day, within a period of 7 days of irregular administration, calculated from a first day on which a tablet has not been taken after at least 7 days of uninterrupted administration (28th day). The last day within this 7-day period is not followed by an at least 7-day period of time in which tablets are taken without interruption since tablets were not taken on the 35th, the 36th and on the 37th days either. The missed administration period is 10 days in this case since it extends from the 28th day to the 37th day. The first day on which additional contraceptive measures are required is the 8th day which follows the abovementioned 7-day period of irregular administration starting from the 28th day. This day is the 35th day since the 7-day period of irregular administration ends on the 34th day. The need for additional contraceptive measures lasts until a period of at least 7 days of uninterrupted administration has again elapsed. Therefore, the period in which additional contraceptive measures are required lasts until the 44th day since 7 days of uninterrupted administration is first reached on the 44th day. Therefore, the warning symbol for lack of contraception is activated from the 35th day to the 44th day.

FIG. 22c shows an example of administration in which the tablets have not been taken on the 34th, 35th, 36th and 37th days and again on the 40th day. In this case, additional contraceptive measures are not required: tablets are not taken on 5 days, specifically on the 34th day, on the 35th day, on the 36th day, on the 37th day and on the 40th day, within a missed administration period of 7 days, calculated from a first day on which a tablet has not been taken after at least 7 days of uninterrupted administration (34th day). The last day within this 7-day missed administration period, that is to say the 40th day, is followed by an at least 7-day period of time in which tablets are taken without interruption (starting from the 41st day). Therefore, the warning symbol is not activated.

FIG. 22d shows an example of administration in which the tablets have not been taken on the 34th, 35th, 36th and 37th days and then again on the 41st day. Additional contraceptive measures are required in this case: Tablets have not been taken on 4 days, specifically on the 34th day, on the 35th day, on the 36th day and on the 37th day, within a period of 7 days of irregular administration, calculated from a first day on which a tablet has not been taken after at least 7 days of uninterrupted administration (34th day). The last day within this 7-day period (40th day) of irregular administration is not followed by an at least 7-day period of time in which tablets are taken without interruption since a tablet is not taken on the 41st day either. The missed administration period actually lasts 8 days. The first day on which additional contraceptive measures are required is the 8th day which follows the abovementioned 7-day period of irregular administration. This day is the 41st day since the 7-day period of irregular administration ends on the 40th day. The need for additional contraceptive measures lasts until a period of at least 7 days of uninterrupted administration has elapsed again. Therefore, the period in which additional contraceptive measures are required lasts until the 48th day since 7 days of uninterrupted administration is first reached on the 48th day. Therefore, the warning symbol for lack of contraception is activated from the 41st day to the 48th day.

What is claimed is:

1. A display device for a dispenser of medicament portions, the display device comprising a display that includes:
    a first display region that comprises first indicator segments, wherein
        a first reference administration time is associated with a first medicament portion of the medicament portions being dispensed,
        a second reference administration time is associated with a calculated time that a second medicament portion of the medicament portions is recommended to be dispensed,
        an administration interval represents a time difference between the first reference administration time and the second reference administration time, and
        an indicator interval represents the administration interval divided by a number of the first indicator segments; and
    an electronic actuator for the display, wherein
        responsive to a first iteration of the indicator interval elapsing, a first indicator segment of the first indicator segments is filled with a first indicator zone; and
        wherein responsive to a next iteration of the indicator interval elapsing, a next indicator segment of the first indicator segments is filled with a next indicator zone;
        wherein the display further includes a second display region that comprises second indicator segments, wherein a second indicator segment of the second indicator segments is displayed within the second reference administration time and a third iteration of the indicator interval elapses after occurrence of the second reference interval; and
        wherein the first display region is a first ring and the second display region is a second ring.

2. The display according to claim 1, wherein the first display region is concentric with the second display region and the first display region surrounds the second display region.

3. The display device according to claim 1, wherein responsive to the second medicament failing to be dispensed within the second reference administration time, the display further comprises a warning symbol.

4. The display according to claim 3, characterized in that each of the first indicator segments and/or the second indicator segments corresponds to periods of time of equal magnitude.

5. The display according to claim 4, characterized in that each of the first indicator segments and/or each of the second indicator segments corresponds to 1 hour.

6. The display according to claim 1, wherein the at least one first display region and the at least one second display region are adjacent to one another.

7. The display according to claim 1, wherein responsive to the second medicament being dispensed prematurely, a subset of the first indicator segments that correspond to negative time are to indicate time left until the second reference administration time.

8. The display according to claim 7, wherein responsive to a current time reaching the second reference administration time, resetting the subset of the first indicator segments to remove a fill.

9. The display according to claim 1, wherein the display further includes a second display region is formed by at least one second indicator segment.

10. The display portions according to claim 9, characterized in that at least two second indicator segments are provided, and in that the second indicator segments are successively switched on as time progresses.

11. The display according to claim 1, wherein at least two first indicator segments are successively switched on as time progresses.

12. The display device according to claim 1, wherein the medicament portions (Ta) are contraceptive portions.

13. The display according to claim 12, characterized in that 20 µg of ethinylestradiol and 3 mg of drospirenone are contained in each medicament portion.

14. The display device according to claim 1, wherein the medicament portions (Ta) are hormone preparation portions.

15. The display according to claim 1, wherein the display further includes a second display region that is spatially delimited from the first display region, the second display region including second indicator segments that display a different color than the first indicator segments.

16. The display according to claim 1, wherein the display further includes a number of medicament portions contained in the dispenser.

17. The display according to claim 1, wherein the display further includes a number of medicament portions which have already been taken in an administration cycle.

18. The display according to claim 1, wherein the display further includes a symbol for interruption in administration.

19. The display according to claim 18, wherein the symbol for interruption in administration includes a number of days for which administration is interrupted.

20. The display according to claim 18, wherein the first display region indicates a period of time which has elapsed between two reference administration times.

21. The display according to claim 1, wherein the display further includes a warning symbol for lack of contraception.

22. The display according to claim 1, wherein the display device is an LCD display device.

23. The display according to claim 1, wherein the display device is a digital display device.

24. A display device for a dispenser of medicament portions, the display device comprises a display that includes:
a first display region that comprises first indicator segments, wherein
a first reference administration time is associated with a first medicament portion of the medicament portions being dispensed,
a second reference administration time is associated with a calculated time that a second medicament portion of the medicament portions is recommended to be dispensed,
an administration interval represents a time difference between the first reference administration time and the second reference administration time, and
an indicator interval represents the administration interval divided by a number of the first indicator segments; and
an electronic actuator for the display, wherein
responsive to a first iteration of the indicator interval elapsing, a first indicator segment of the first indicator segments is filled with a first indicator zone;
wherein responsive to a next iteration of the indicator interval elapsing, a next indicator segment of the first indicator segments is filled with a next indicator zone;
wherein the display further includes a second display region that comprises second indicator segments, wherein a second indicator segment of the second indicator segments is displayed responsive to the second medicament portion failing to be dispensed within the second reference administration time and a third iteration of the indicator interval elapses after occurrence of the second reference interval; and
wherein the first display region includes at least one first ring for the first indicator segments, the second display region includes at least one second ring for the second indicator segments, and the first indicator segments and the second indicator segments are concentric to one another.

25. A display device for a dispenser of medicament portions, the display device comprises a display that includes:
a first display region that comprises first indicator segments, wherein
a first reference administration time is associated with a first medicament portion of the medicament portions being dispensed,
a second reference administration time is associated with a calculated time that a second medicament portion of the medicament portions is recommended to be dispensed,
an administration interval represents a time difference between the first reference administration time and the second reference administration time, and
an indicator interval represents the administration interval divided by a number of the first indicator segments; and
an electronic actuator for the display, wherein
responsive to a first iteration of the indicator interval elapsing, a first indicator segment of the first indicator segments is filled with a first indicator zone; and
wherein responsive to a next iteration of the indicator interval elapsing, a next indicator segment of the first indicator segments is filled with a next indicator zone,
wherein the display further includes a warning symbol for lack of contraception;
wherein the warning symbol is displayed on the display if the following conditions are met:

a) failure to administer at least one medicament portion on at least one day results in a missed administration period which is defined by
   i) the missed administration period following a first administration period of at least 7 days of uninterrupted administration of medicament portions,
   ii) the missed administration period again being followed by a second administration period of at least 7 days of the uninterrupted administration of medicament portions,
   iii) no medicament portion being taken on at least one day in the missed administration period,
   iv) no period of at least 7 days of uninterrupted administration being included in the missed administration period,
   v) no medicament portion being taken on a first and last day of the missed administration period, and
   vi) the missed administration period lasting longer than 7 days;
b) the first day on which the warning symbol appears is an 8th day of the missed administration period;
c) the last day on which the warning symbol appears is a 7th day of the second administration period which follows the missed administration period and which involves uninterrupted administration of medicament portions.

* * * * *